United States Patent
Hidaka et al.

(10) Patent No.: US 9,592,149 B2
(45) Date of Patent: Mar. 14, 2017

(54) HEAT GENERATING EYE MASK

(75) Inventors: Yuki Hidaka, Tokyo (JP); Kazuo Ohashi, Tokyo (JP); Kyouko Tagami, Tokyo (JP); Takeshi Oka, Tokyo (JP); Ryuichi Noki, Tokyo (JP); Takashi Higashi, Tokyo (JP)

(73) Assignee: Kao Corporation, Tokyo (JP)

( * ) Notice: Subject to any disclaimer, the term of this patent is extended or adjusted under 35 U.S.C. 154(b) by 899 days.

(21) Appl. No.: 12/675,121

(22) PCT Filed: Nov. 6, 2008

(86) PCT No.: PCT/JP2008/070170
§ 371 (c)(1),
(2), (4) Date: Feb. 25, 2010

(87) PCT Pub. No.: WO2009/060883
PCT Pub. Date: May 14, 2009

(65) Prior Publication Data
US 2010/0241199 A1 Sep. 23, 2010

(30) Foreign Application Priority Data

Nov. 9, 2007 (JP) .................................. 2007-291653
Jul. 4, 2008 (JP) .................................. 2008-176182

(51) Int. Cl.
A61F 7/03 (2006.01)
A61F 7/00 (2006.01)
A61F 7/02 (2006.01)

(52) U.S. Cl.
CPC ...... A61F 7/034 (2013.01); *A61F 2007/0004* (2013.01); *A61F 2007/0029* (2013.01);
(Continued)

(58) Field of Classification Search
CPC ...... A61F 2007/0029; A61F 2007/0039; A61F 2007/0226; A61F 2007/0268; A61F 7/034;
(Continued)

(56) References Cited

U.S. PATENT DOCUMENTS 6,139,486 A * 10/2000 Matuszewski et al. ........ 600/15
6,139,929 A    10/2000 Hayton et al.
(Continued)

FOREIGN PATENT DOCUMENTS

CN      1373649 A     10/2002
CN      2730154 Y     10/2005
(Continued)

OTHER PUBLICATIONS

Office Action issued on Oct. 11, 2011 in the corresponding European Application No. 08 846 923.4.
(Continued)

*Primary Examiner* — Jaymi Della
(74) *Attorney, Agent, or Firm* — Oblon, McClelland, Maier & Neustadt, L.L.P.

(57) ABSTRACT

A heat generating device includes a heat generating element enclosed in an air-permeable stretch bag. The heat generating element includes an air-permeable first side adapted to be located proximal to the skin of a wearer, a second side adapted to be located distal to the skin of a wearer, and a heat generating member interposed between the first side and the second side. It is preferred that a part of the heat generating element is fixed to a part of the inner side of the stretch bag in the overlap between the stretch bag and the heat generating element in a plan view of the heat generating device.

22 Claims, 12 Drawing Sheets

(52) U.S. Cl.
CPC ............... *A61F 2007/0039* (2013.01); *A61F 2007/0062* (2013.01); *A61F 2007/0226* (2013.01); *A61F 2007/0228* (2013.01); *A61F 2007/0268* (2013.01)

(58) Field of Classification Search
CPC ...... A61F 2007/0002; A61F 2007/0003; A61F 2007/0004; A61F 2007/0006; A61F 2007/0228; A61F 2007/023; A61F 2007/0231
USPC ........................... 607/108, 109, 114, 96, 112
See application file for complete search history.

(56) References Cited

U.S. PATENT DOCUMENTS

| | | | |
|---|---|---|---|
| 6,409,746 B1 * | 6/2002 | Igaki et al. | 607/109 |
| 7,707,655 B2 * | 5/2010 | Braunecker et al. | 2/206 |
| 2005/0192653 A1 * | 9/2005 | Tsunakawa et al. | 607/109 |
| 2007/0256679 A1 | 11/2007 | Yim et al. | |
| 2008/0269850 A1 * | 10/2008 | Dodo | 607/96 |
| 2010/0010598 A1 * | 1/2010 | Igaki et al. | 607/109 |
| 2010/0023099 A1 | 1/2010 | Hidaka et al. | |

FOREIGN PATENT DOCUMENTS

| | | | | |
|---|---|---|---|---|
| CN | 101820836 B | | 10/2012 | |
| EP | 1 293 199 A1 | | 3/2003 | |
| EP | 1 782 768 A1 | | 5/2007 | |
| JP | 6-61222 | | 8/1994 | |
| JP | 3053336 | | 8/1998 | |
| JP | 2000-139992 | | 5/2000 | |
| JP | 2001 514712 | | 9/2001 | |
| JP | 2002-45386 A | | 2/2002 | |
| JP | 2002-45387 | | 2/2002 | |
| JP | 2002-65714 | | 3/2002 | |
| JP | 2005058744 A | * | 3/2005 | |
| JP | 2006-51191 | | 2/2006 | |
| JP | 2006 167253 | | 6/2006 | |
| JP | 2006-167253 | | 6/2006 | |
| JP | 2006-204733 A | | 8/2006 | |
| JP | 2007-14792 | | 1/2007 | |
| JP | 2007 14792 | | 1/2007 | |
| JP | 2007 98092 | | 4/2007 | |
| JP | 2007-98092 | | 4/2007 | |
| JP | 2007-185398 A | | 7/2007 | |
| JP | 02009061166 A | * | 9/2007 | |
| JP | 2007-289682 A | | 11/2007 | |
| WO | 2006 006657 | | 1/2006 | |
| WO | 2006/006664 | * | 1/2006 | ............... A61F 7/08 |
| WO | WO 2006/006656 | | 1/2006 | |
| WO | WO 2006/006657 A1 | | 1/2006 | |
| WO | WO 2007004309 A1 | * | 1/2007 | |
| WO | WO 2007/114352 A1 | | 10/2007 | |

OTHER PUBLICATIONS

Office Action issued Sep. 30, 2011 in Chinese Patent Application No. 200880110774.2 (with English translation).
Office Action issued Nov. 20, 2012 in Japanese Application No. 2008-176182 (With English Translation).
Office Action issued Feb. 12, 2013 in Japanese Application No. 2008-176182 (With English Translation).
U.S. Appl. No. 14/364,165, filed Jun. 10, 2014, Oka.
U.S. Appl. No. 14/405,943, filed Dec. 5, 2014, Oka, et al.
Japanese Office Action Issued Aug. 7, 2012 in Patent Application No. 2008-176182 (with English translation).

* cited by examiner

HEAT GENERATING EYE MASK

PRIORITY INFORMATION

This application is a 371 of International Application No. PCT/JP08/70170, filed Nov. 6, 2008, and claims foreign priority to Japanese Patent Application No. 2007-291653, filed Nov. 9, 2007, and Japanese Patent Application No. 2008-176182, filed Jul. 4, 2008.

TECHNICAL FIELD

The present invention relates to a heat generating device used to warm a human body.

BACKGROUND ART

Various heat generating devices having a heat generating material sealed in an air-permeable flat bag which are used to warm a human body by the heat generated by the heat generating material are known. The heat generating device has an adhesive applied to the outer side thereof so that the device may be attached to a body or clothing of a wearer. When a heat generating device of this type is attached to a movable part of a wearer's body, such as a joint, it is likely that the heat generating device fails to sufficiently conform to the movement of the part, which can cause the adhesive to separate from the adherend or cause uncomfortable skin tightness to the wearer.

To avoid this, a stretch member can be used in heat generating device. For example, Patent Document 1 discloses a disposable body warmer attached to a stretch member or a plurality of disposable body warmers connected as wrapped in a stretch member so that the disposable body warmer may have a good fit against a human body. Patent Document 2 discloses a stretchable heat generating device having a bag formed of a stretch material and a heat generating element sealed in the bag. The assignee of the present invention has proposed a warming device having a heat generating portion having a plurality of heat generating parts, in which the heat generating portion includes a stretch part so that the heat generating portion may stretch between every heat generating parts (see Patent Document 3). However, any of the above described devices has a limited stretchable portion because the stretch part is only formed between heat generating parts or elements. Moreover, when a stretch member directly covers a heat generating element, the stretch of the stretch member is hindered. Therefore, the warming devices described in these patent documents are, while stretchable, not always sufficiently follow the movement of a moving part of a wearer.
Patent Document 1 JP 6-61222U
Patent Document 2 JP 2006-51191A
Patent Document 3 JP 2000-139992A

DISCLOSURE OF THE INVENTION

The present invention provides a heat generating device including an air-permeable stretch bag and a heat generating element enclosed in the bag. The heat generating element has a first side which is air-permeable and adapted to be located proximal to a wearer's body, a second side which is adapted to be located distal to a wearer's body, and a heat generating member interposed between the first and second sides. The heat generating element is fixed to the inner side of the stretch bag in such a manner that the stretchability of the stretch bag is not impaired.

DETAILED DESCRIPTION OF THE INVENTION

Figure 1:
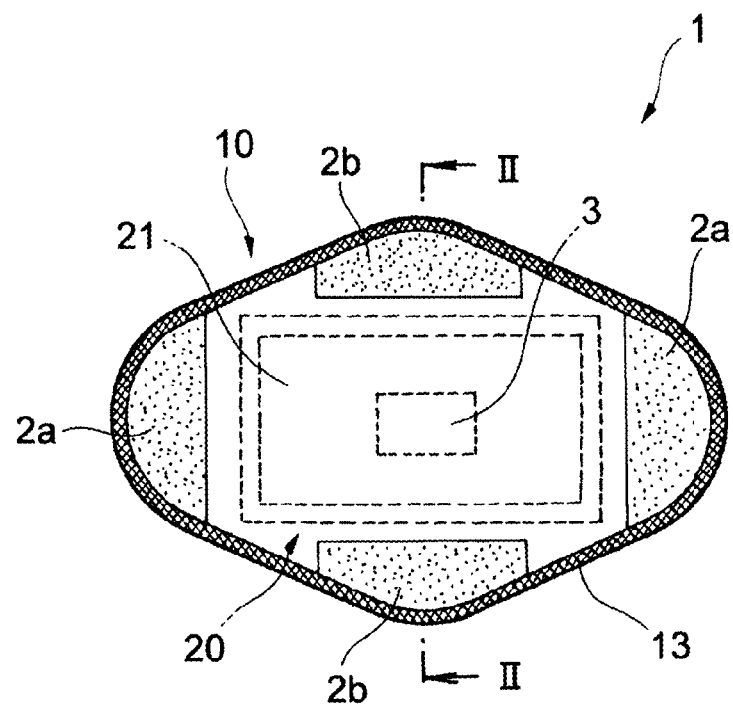
FIG. 1 is a plan of a heat and steam generating device as a preferred embodiment of the heat generating device of the invention.
Figure 2:
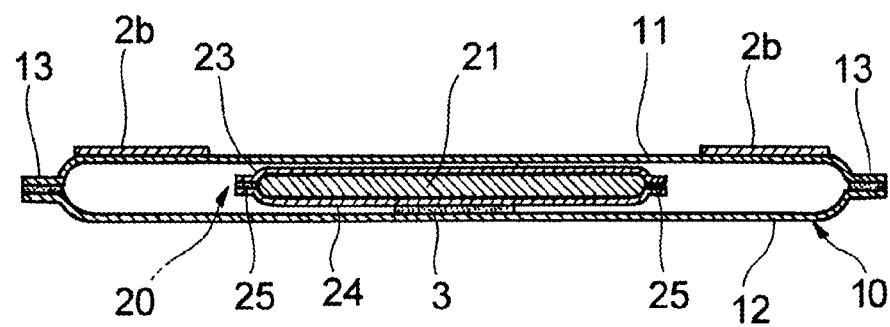
FIG. 2 is a cross-section taken along line II-II in FIG. 1.

The present invention will be described based on its preferred embodiments with reference to the accompanying drawing. FIG. 1 is a plan of a heat and steam generating device 1 as an embodiment of the heat generating device of the invention. FIG. 2 is a cross-section taken along line II-II in FIG. 1. The heat and steam generating device 1 of the present embodiment is basically composed of a bag 10 and a heat generating element 20. The heat generating element 20 is enclosed in the bag 10. The heat and steam generating device 1 of the present embodiment is used as attached directly to a part of body of a wearer. The heat and steam generating device 1 includes a heat generating member and is designed to produce steam at a prescribed elevated temperature from the heat generating member and to apply the steam to the wearer's body to improve the physiological function of the wearer.

The bag 10 has a first stretch sheet 11 that is adapted to be located proximal to a wearer's body and a second stretch sheet 12 that is adapted to be located distal to a wearer's body. The two stretch sheets 11 and 12 have the same rounded rhombic shape. The two stretch sheets 11 and 12 are superposed on each other and joined together along their perimeters 13 to make a bag 10 providing a space inside. Therefore, the bag 10 has stretchability.

The first and second stretch sheets 11 and 12 each have stretchability in at least one direction. When the first and second stretch sheets 11 and 12 each have stretchability in only one direction, that direction is preferably coincident with the longer diagonal or the shorter diagonal of the nearly rhombic shape of the bag. When the stretch sheets 11 and 12 each have stretchability in two directions perpendicular to each other, the directions are preferably coincident with the longer diagonal and the shorter diagonal of the nearly rhombic shape of the bag. As used herein, the term "stretch sheet" is intended to include a sheet having at least one of the hereinafter described extensibility and retractability from extension (contractibility). For example, it is only necessary that at least one of the stretch sheets 11 and 12 is unidirectionally extensible. It is preferred that one of the stretch sheets 11 and 12 has extensibility while the other has both extensibility and retractability.

The first stretch sheet 11 of the bag 10 has, on its peripheral portion, attachment means for attaching the heat and steam generating device 1 to a wearer's body. In the present embodiment, a pair of first attachment means 2a are provided at the opposing ends of the longer diagonal of the nearly rhombic bag 10, and a pair of second attachment means 2b are at the opposing ends of the shorter diagonal. The arrangement of the attachment means is not limited to the above described configuration. For example, the attachment means may be provided along the perimeter 13 either continuously or discontinuously. The attachment means 2a and 2b are exemplified by an adhesive.

The heat generating element 20 serves to apply steam generated from its heat generating member at a prescribed elevated temperature to a wearer's body through the bag 10. The heat generating element 20 is rectangular with long sides and short sides. The heat generating element 20 is enclosed in the center of the bag 10 with its longitudinal direction parallel to the longer diagonal of the nearly rhombic bag 10.

As illustrated in FIGS. 1 and 2, the bag 10 is sufficiently larger than the heat generating element 20 in dimension. The stretch sheets 11 and 12 making the bag 10 extend outward from both the long sides and the short sides of the heat generating element 20. While, in the embodiment illustrated in FIGS. 1 and 2, the rectangular heat generating element 20 having long sides and short sides is held in a nearly rhombic bag 10, the bag 10 and the heat generating element 20 may have similar shapes. In addition, the bag 10 and the heat generating element 20 may be for example rhombic, rectangular, elliptical or circular. Furthermore, one bag may have two or more heat generating elements enclosed therein.

Figure 3:
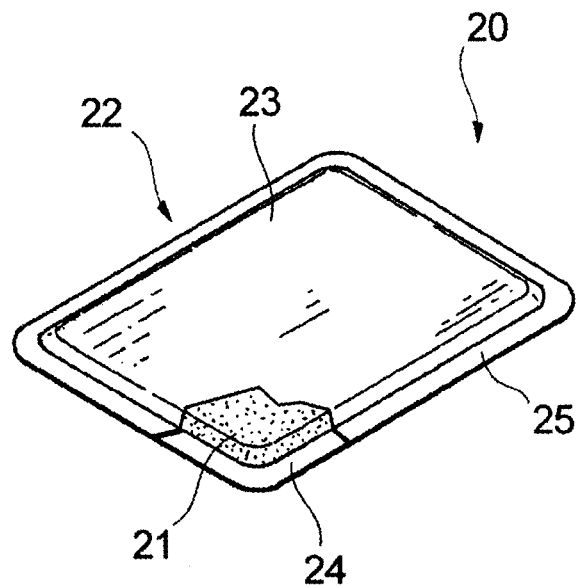
FIG. 3 is a perspective of a heat generating element used in the heat and steam generating device shown in FIG. 1, with part cut away.

As illustrated in FIGS. 2 and 3, the heat generating element 20 includes a heat generating member 21 and a holder 22 holding the heat generating member 21. The holder 22 is flat-shaped and defines the contour of the heat generating member 20. The holder 22 is composed of a plurality of sheet materials joined together to provide a closed space in which the heat generating member 21 is placed. The flat holder 22 has a first side 23 located proximate to the wearer's skin and an opposite, second side 24 located distal to the wearer's skin.

The heat generating member 21 contains an oxidizable metal. The heat generating member 21 is a part that generates steam of prescribed elevated temperature by making use of the heat accompanying the oxidation reaction between the oxidizable metal and oxygen. The details of the heat generating member 21 will be described later in more detail.

The first side 23 has air permeability to allow for passage of air and steam. The second side 24 is less permeable to air and steam than the first side 23. In other words, the second side 24 is sparingly air-permeable or air-impermeable compared with the first side 23. Whether the second side 24 is sparingly air-permeable or air-impermeable is selected as appropriate for the intended use of the heat and steam generating device 1 or the amount of steam generated from the heat and steam generating device 1.

The heat generating element 20 is used with its first side 23 facing a wearer's body and the second side 24 facing wearer's clothing. The heat and steam generating device 1 is thus configured to apply steam generated by the heat generation of the heat generating member 21 to the wearer's skin through the first side 23 and the bag 10.

Each of the first side 23 and the second side 24 of the heat generating element 20 is formed of a sheet material. The periphery of the sheet material forming the first side 23 and that forming the second side 24 are bonded to each other so that the holder 22 of the heat generating element 20 has a closed loop of a peripheral joint 25. The peripheral joint 25 is continuous. The first side 23 and the second side 24 of the holder 22 are not bonded to each other in the region inside the peripheral joint 25. By this configuration, the holder 22 provides a single closed space in which the heat generating member 21 can be enclosed. As illustrated in FIGS. 2 and 3, the heat generating member 21 put into the space formed by the holder 22 occupies practically the whole space of the holder 22. To put it another way, the holder 22 contains one heat generating member 21, and the heat generating member 21 occupies practically the whole area of the holder 22 except the peripheral joint 25. While in FIG. 2 the heat generating member 21 is merely placed in the closed space of the holder 22, the heat generating member 21 and a part of the inner side of the holder 22 may be fixed to each other by means for fixing, such as an adhesive, in a manner that does not interfere with heat generation.

The heat generating element 20 is fixed to the inner side of the bag in such a manner that the stretchability of the stretch bag 10 is not impaired. The heat generating element 20 is thus prevented from moving out of place inside the bag 10 during transfer or use. The position of fixing the heat generating element 20 to the bag 10 is not limited as long as the stretchability of the bag 10 is not diminished. Nevertheless, it is preferred that the position of fixing is such that the bag 10 is stretchable in the overlap with the heat generating element 20 in a plan view; for such a design allows the bag 10 to have a large stretchable portion. Specifically, as shown in FIGS. 1 and 2, it is preferred that part of the heat generating element 20 is fixed to part of the inner side of the bag 10 within the overlap between the bag 10 and the heat generating element 20 in a plan view of the heat and steam generating device 1. The fixing part is indicated as numerical reference 3 in FIGS. 1 and 2. The fixing part 3 is located at virtually the center of the bag 10 and that of the heat generating element 20. There is only one fixing part 3 for one heat generating element 20.

In the present embodiment, the heat generating element 20 is preferably fixed to the inner side of the stretch sheet 12 that faces the second side of the heat generating element 20. Numeral 3 indicates the fixing part at which the bag 10 and the heat generating element 20 are fixed to each other. That is, the fixing part 3 is preferably provided between the stretch sheet 12 of the bag 10 and heat generating element 20. In this case, the heat and steam generating device 1 exhibits conformability to the wearer's movement and apply the heat and steam generated from the heat generating element 20 to the wearer's body satisfactorily. The area of the fixing part 3 influences the stretchability of the bag 10. If the fixing part 3 has too large an area, the bag 10 has a so decreased stretchable portion. Conversely, the fixing part 3 with too small an area can fail to securely fix the heat generating element 20 to the bag 10. For these considerations, the area of the fixing part 3 is preferably not more than 30%, more preferably 20% or less, even more preferably 15% or less, of the plan view area of the bag 10 and preferably at least 1%, more preferably 5% or more, of the plan view area of the heat generating element 20. The recited preferred range of the area of the fixing part 3 is particularly favorable in the case where the fixing part 3 overlaps the heat generating element 20 as described infra; for the fixing part 3 neither reduces the air permeability of the bag 10 nor interferes with heat generation of the heat generating element 20.

When the heat generating element 20 is fixed to the bag 10 at its portion inward of its periphery (e.g., at the center thereof), it is preferred that the fixing part 3 is so shaped as to have no or small anisotropy in order to minimize the interference of the fixing part 3 with the stretch of the bag 10. Exemplified shape with no anisotropy is a circle and a regular polygon. Exemplified shape with small anisotropy is a rectangle or an ellipse each having a longest dimension to shortest dimension ratio of 5 or less, preferably 3 or less. As long as the stretchability is not impaired, there may be two or more fixing parts per heat generating element.

On the other hand, where the fixing part 3 is provided on the periphery of the heat generating element 20, the fixing part 3 may have a shape with large anisotropy (e.g., an oblong rectangle) as long as the anisotropy is in a direction perpendicular to the most extensible direction of the bag 10. That is, as long as the longitudinal direction of the fixing part 3 is perpendicular to the extensible direction of the bag 10, such geometry of the fixing part does not cause any hindrance to the extension of the bag 10.

Figure 4:
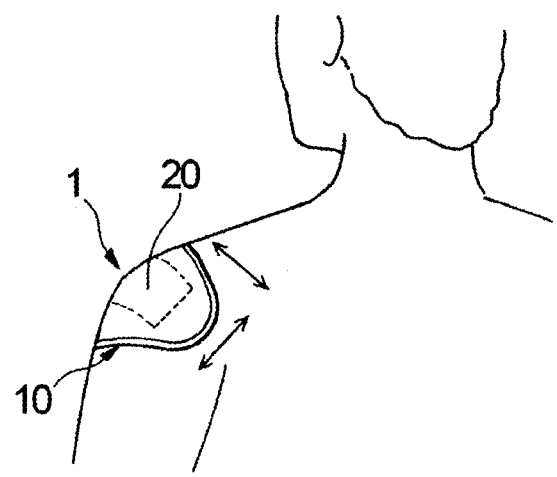
FIG. 4 illustrates a usage of the heat and steam generating device shown in FIG. 1.

In the present embodiment, the stretch bag 10 is extensible and retractable in not only the portions outside the long sides and the short sides of the heat generating element 20 but also the overlap with the heat generating element 20 except the fixing part 3. Accordingly, the bag 10 has a large stretchable portion. As a result, when the heat and steam generating device 1 of the present embodiment is applied to a moving part of a wearer, such as a joint, for example, when it is attached to a wearer's shoulder as illustrated in FIG. 4, the bag 10 of the heat and steam generating device 1 freely stretches and contracts in conformity to the wearer's motion thereby providing a good fit. Since the heat generating element 20 is fixed to the inner side of the bag 10, it is prevented from moving out of position and kept at the intended position where to apply steam. In this regard, the stretchability of the bag 10 is lost in the fixing part 3 as a result of the provision of the fixing part 3, so the bag 10 does not substantially stretch in the fixing part 3. In order to fix the fixing part 3 to the bag 10, the fixing part 3 can be formed, for example, with an adhesive or by heat sealing.

When use in the manner illustrated in FIG. 4, the heat with the steam at a prescribed elevated temperature is applied directly to the wearer's body in the present embodiment of the heat and steam generating device 1. Because heat accompanied by steam generation is transmitted at a higher rate so that it is more capable of increasing the body temperature in depths than heat not accompanied by steam generation. A rise in temperature deep in the body stimulates the heat center, warm-sensitive receptor, via the autonomic nerves. It follows that blood vessels dilate so as to increase the blood flow and to rise the peripheral temperature. In short, use of the heat and steam generating device 1 brings about improvements on various physiological functions. For instance, the usage illustrated in FIG. 4 alleviates shoulder joint pains due to stiff shoulder, frozen shoulder, and dislocation. The heat and steam generating device 1 is also applicable to any other parts of human body, particularly actively moving parts such as knees, ankles, elbows, and arms, to ease the joint pain.

Materials making each member constructing the heat and steam generating device 1 will be described. The first and second stretch sheets 11 and 12 making the bag 10 are not particularly restricted in material as long as they are stretchable and air permeable. Particularly the first stretch sheet 11 is preferably of material having good feel to the touch since the first stretch sheet 11 is to be brought into direct contact with a wearer's skin. The material of the stretch sheets are, for example, synthetic fibers including polyesters such as polyethylene terephthalate (PET), polyolefins such as polyethylene (PE) and polypropylene (PP), polyamide, and polyacrylate; naturally occurring fibers such as cellulose, silk, cotton, and wool; or composite fibers thereof. The nonwoven fabrics may be formed of one or more kinds of fibers described above by through-air bonding, spun-bonding, needle punching, melt-blowing, carding, thermal fusion bonding, hydroentanglement, solvent bonding, and the like. Not only nonwoven fabrics but knitted fabrics are also usable. In view of hand and elasticity, the stretch sheets suitable for use in the present invention are preferably formed of stretch nonwoven fabrics. Preferred stretch nonwoven fabrics are exemplified by through-air nonwoven fabrics or spun-bonded nonwoven fabrics containing elastic fibers (e.g., polyurethane fibers or polyester fibers). Nonwoven fabrics surface treated with silicone or a surface active agent are also useful in view of the feel to the touch. The two stretch sheets 11 and 12 may be of the same or different kinds.

Additionally, each of the stretch sheets 11 and 12 preferably has a load of 5N/2.5 cm or less, more preferably 3N/2.5 cm or less, even more preferably 1N/2.5 cm or less, at 50% extension in the most stretchable direction. The load at 50% extension in the most stretchable direction set in the range recited, the sheets stretch largely with small force, so that the skin tightness experienced by a wearer in moving the body to which the heat and steam generating device 1 is attached can be reduced. There is no lower limit to that load. The smaller the load, the more comfortable increase.

The load at 50% extension is measured as follows. The stretch sheet is cut to 10 cm in the most extensible direction and 2.5 cm in the direction perpendicular to the most extensible direction to obtain a rectangular test piece. The test piece is set on a tensile tester at an initial jaw separation of 5 cm and extended at a rate of 10 cm/min. The load is read at 50% extension (when the test piece is extended to 1.5 times the initial length). Measurements were taken in triplicate to obtain an average.

Further, each of the stretch sheets 11 and 12 preferably has a load of 15N/2.5 cm or less, more preferably 10N/2.5 cm or less, even more preferably 5N/2.5 cm or less, at 50% extension in the least stretchable direction. The load at 50% extension in the least stretchable direction set in the range recited, the skin tightness experienced by a wearer can be reduced when the wearer moves a part of body to which the heat and steam generating device 1 is attached by twisting as well as bending. The load at 50% extension in the least stretchable direction is measured in the similar manner as described above.

It is preferred for the stretch sheets 11 and 12 to have not only the above-described loads at 50% extension but a residual strain of 50% or less, more preferably 40% or less, even more preferably 30% or less, when 50% extended in the most extensible direction and released. With these conditions fulfilled, the heat and steam generating device 1 attached to a wearer's body exerts adequate retractability to provide improved fit. From the same viewpoint, the stretch sheets 11 and 12 preferably have a residual strain of 80% or less, more preferably 75% or less, even more preferably 70% or less, when 50% extended in the least extensible direction and released. The residual strain is measured as follows. The load L1 at 50% extension is measured in accordance with the method described above. After the test piece is retracted to the initial length at the same rate, it is again extended to read the load L2 at 50% extension. The ratio of the first and second loads L1 and L2 is calculated from formula (1) to give a residual strain. Measurements were taken in triplicate to obtain an average.

$$\text{Residual strain} = (L1 - L2)/L1 \times 100(\%) \quad (1)$$

To obtain a heat generating device that conforms to the wearer's movement and provides good fit and comfort, it is preferred that at least one of the stretch sheets 11 and 12 has extensibility whilst the other has both extensibility and retractability (recovery from extension). It is more preferred that the stretch sheet 12 distal to a wearer's body has extensibility and retractability. In another preferred form, it is preferred for the stretch sheet 12 to be stretchable in perpendicularly crossing two directions and to have extensibility and retractability.

In the case where the stretch sheets 11 and 12 are nonwoven fabrics, it is advisable to properly select the basis weight and thickness of the stretch sheets 11 and 12 and the thickness of the constituent fibers so as to provide a pleasant feel to the skin. From this standpoint, the nonwoven fabric making the stretch sheets 11 and 12 preferably has a basis weight of 10 to 200 $g/m^2$, more preferably 20 to 130 $g/m^2$. In terms of heat insulation and prevention of dew condensation, the stretch sheet 12 preferably has a basis weight of 30 $g/m^2$ or more. The stretch sheet 11 preferably has a basis weight of 130 $g/m^2$ or less in terms of feeling of warmth. It is preferred that the basis weight of the stretch sheet 12 distal to the wearer's body is equal to or larger than that of the stretch sheet 11 proximal to the wearer's body in terms of heat insulation, feeling of warmth in use, and comfort of use.

The heat generating element 20 will then be described. The heat generating element 20 has properly controlled air permeances through the first side 23 and the second side 24 so that steam may be released preferentially through the first side 23. Specifically, the second side is designed to have a higher air permeance than the first side. The term "air permeance" as used herein is a value measured in accordance with JIS P8117, which is defined to be the time required for 100 ml of air to pass through an area of 6.42 $cm^2$ under a constant pressure. A higher air permeance means more time needed for air passage, i.e., lower air permeability. Conversely, a lower air permeance means higher air permeability. Air permeance as defined above and air permeability are in a converse relation. Comparing the air permeability between the first side 23 and the second side 24 in the present embodiment, the first side 23 has equal or higher air permeability than the second side 24 so that the steam may be released preferentially through the first side 23. That is, as previously stated, the second side 24 is air impermeable or sparingly air permeable (i.e., air permeable but less air permeable than the first side 23).

The holder 22 has a flat shape having the air permeable first side 23 and the opposite, air impermeable second side 24 and is designed to cause steam and heat generation through the air permeable first side 23. Alternatively, the holder 22 has a flat shape having the air permeable first side 23 and the opposite, sparingly air permeable second side 24 and is designed to cause steam and heat generation through the air permeable first side 23. In the case where the second side 24 is sparingly air permeable, the air permeance of the first side 23 and that of the second side 24 should be controlled so that air may enter the holder 22 preferentially through the second side 24 while steam may be released preferentially through the first side 23.

In the case where the second side 24 is sparingly air permeable, it is preferred that the air permeance of the second side 24 is 5 or more times, more preferably 10 or more times, that of the first side 23 in order to suppress steam release through the second side 24 while securing an air inflow through that side. It is otherwise preferred that the ratio of the air permeance of the first side 23 to that of the second side 24 (first side/second side ratio) is 0.5 or smaller, more preferably 0.2 or smaller. By so controlling the air permeance, release of steam from the second side 24 can be further reduced while further increasing release of steam from the first side 23. In the case where the second side 24 is air impermeable, on the other hand, air supply into the holder 22 and release of steam are exclusively done through the first side 23.

When the second side 24 is sparingly air permeable, the air permeance of the second side 24 is preferably 5000 sec/100 ml or more, more preferably 10000 sec/100 ml or more, even more preferably 20000 sec/100 ml or more, still more preferably 30000 sec/100 ml or more. On the other hand, the air permeance of the first side 23 is preferably 1000 to 50000 sec/100 ml irrespective of whether the second side 24 is air impermeable or sparingly air permeable.

Each of the first side 23 and the second side 24 of the heat generating element 20 is formed of a sheet material. Sheet materials that govern air permeance and prevent powder from leaking include melt blown nonwoven fabric and moisture permeable film. Moisture permeable film is obtainable by melt molding a mixture of a thermoplastic resin and an organic or inorganic filler incompatible with the resin into film and uniaxially or biaxially stretching the film to develop a finely porous structure. Sheet materials having different air permeances and water vapor transmission rates can be combined to make a laminate sheet. Use of such laminate sheets enables free control of air permeances of the first side 23 and the second side 24.

The heat generating member 21 of the heat generating element 20 will be described. The heat generating member 21 contains an oxidizable metal, a reaction accelerator, an electrolyte, and water. The heat generating member 21 has, for example, the form of heat generating sheet or powder. In the case when the heat generating member 21 is a heat generating sheet, it is preferably a water-containing fibrous sheet containing an oxidizable metal, a reaction accelerator, a fibrous material, an electrolyte, and water. The heat generating sheet is more preferably a molded sheet containing an oxidizable metal, a reaction accelerator, and a fibrous material and having incorporated therein an aqueous electrolyte solution. The heat generating sheet is exemplified by a sheet formed by a wet papermaking technique and a laminate structure in which heat generating powder is held in between sheets of paper, etc. Such a heat generating sheet is produced by, for example, the wet papermaking process taught in commonly assigned JP 2003-102761A or extrusion using a die coater. In the case when the heat generating member 21 is heat generating powder, it is preferably composed of an oxidizable metal, a reaction accelerator, a moisture retaining agent, an electrolyte, and water. A heat generating sheet is preferred to a heat generating powder in terms of even application of steam whatever posture a wearer takes. Furthermore, a heat generating sheet is advantageous over a heat generating powder in terms of ease of smoothing out the exothermic temperature and high ability to hold an oxidizable metal.

The heat generating member 21 which is a heat generating sheet is preferably a molded sheet made out of 60% to 90% of an oxidizable metal, 5% to 25% of a reaction accelerator, and 5% to 35% of a fibrous material, all by weight, having incorporated therein 30 to 80 parts by weight, per 100 parts by weight of the molded sheet, of a 1% to 15% by weight aqueous solution of an electrolyte. On the other hand, the heat generating member 21 which is a heat generating powder is preferably a mixture of 20% to 50%, more preferably 25% to 40%, of an oxidizable metal, 3% to 25%, more preferably 5% to 20%, of a reaction accelerator, 3% to 25%, more preferably 5% to 20%, of a moisture retaining agent, all by weight, and 20 to 70 parts by weight, more preferably 30 to 60 parts by weight, per 100 parts by weight of the solids content including the oxidizable metal, reaction accelerator, and moisture retaining agent, of a 0.3% to 10%, more preferably 0.5% to 5%, by weight aqueous solution of an electrolyte. The materials constituting the heat generating sheet or heat generating powder can be selected from those commonly used in the art. The materials described in JP 2003-102761A supra are useful as well.

The heat and steam generating device 1 of the present embodiment is packaged in a wrapper (not shown) made of an oxygen barrier material so as to protect the heat generating member 21 from coming into contact with air until use. Materials of such an oxygen barrier wrapper preferably include those having an oxygen transmission rate (ASTM D3985) of 10 cm$^3$·mm/(m$^2$·day·MPa) or lower, more preferably 2 cm$^3$·mm/(m$^2$·day·MPa) or lower. Examples of the oxygen barrier wrapper include a film of an ethylene-vinyl alcohol copolymer, or polyacrylonitrile; and a laminate of such a film and vacuum deposited ceramic or aluminum or the like as well as a single layer film of metal, e.g., aluminum film, or plastic, e.g., a polyolefin.

Second to fifth preferred embodiments of the present invention will then be described with reference to FIGS. 5 through 17. The description on the first embodiment appropriately applies to these embodiments unless otherwise specified. Thus in FIGS. 5 to 17, common members are identified by the same numerals as in FIGS. 1 to 4.

The heat and steam generating device 1 of the second embodiment shown in FIG. 5 has a curved oval-shaped or kidney bean-shaped bag 10. The bag 10 has a first stretch sheet 11 proximal to the wearer's skin and a second stretch sheet 12 distal to the wearer's skin. The two stretch sheets 11 and 12 are superposed on each other and joined together along their perimeters 13. The central portions of the two stretch sheets 11 and 12 along the vertical direction are additionally joined along the vertical centerline L (transverse centerline) of the bag 10 with a certain width to form a central joint 14. As a result, the bag 10 provides two closed spaces of the same shape, in which rectangular heat generating elements 20a and 20b are respectively put. The heat generating elements 20a and 20b are disposed symmetrically about the centerline L. In the embodiment illustrated in FIG. 5, as long as the heat generating elements are fixed at the respective fixing parts, the two stretch sheets 11 and 12 do not need to be joined in the central portion along the vertical (transverse) direction of the bag 10.

Figure 5A:
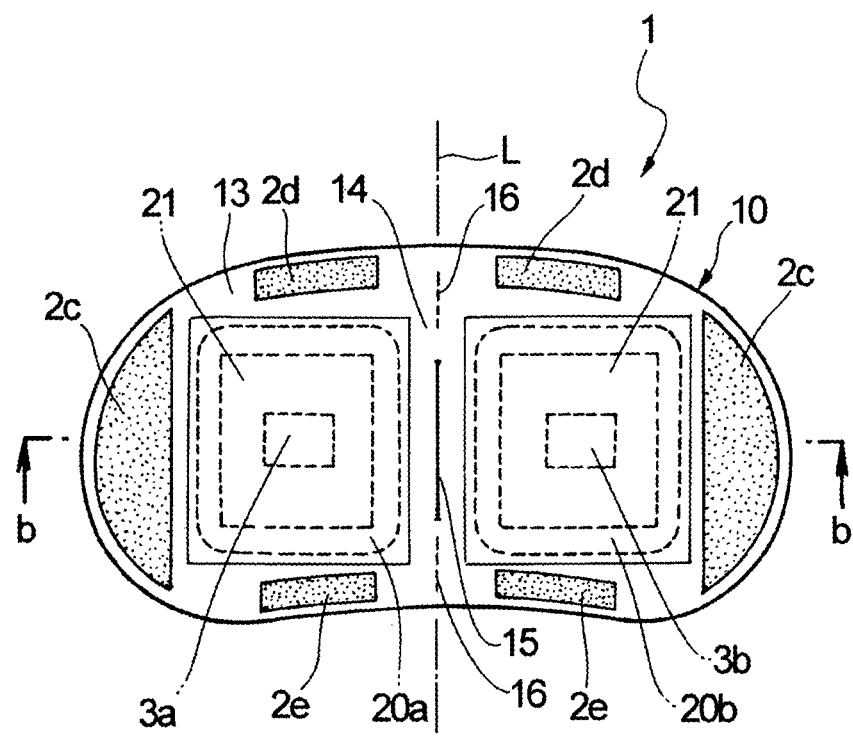
FIG. 5($a$) is a plan of a heat and steam generating device as a second embodiment of the heat generating device of the invention, and FIG. 5($b$) is a cross-section taken along line b-b in FIG. 5($a$).
Figure 5B:
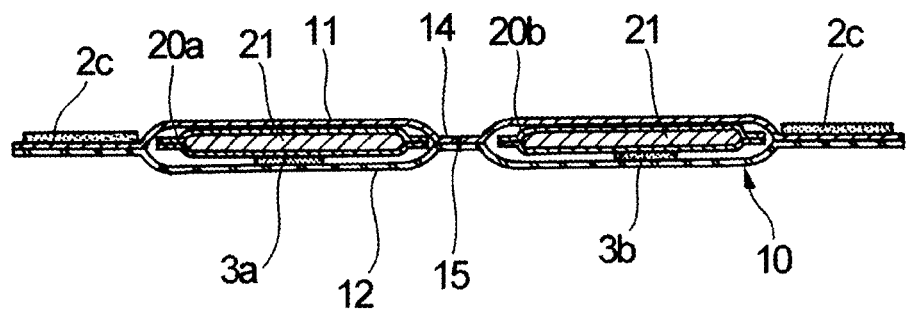

The first stretch sheet 11 has provided thereon attachment means 2c, 2d, and 2e for attaching the heat and steam generating device 1 to a wearer's body. All the attachment means 2c, 2d, and 2e are provided outside the heat generating elements 20a and 20b. As shown in FIGS. 5(a) and 5(b), the attachment means 2c is provided at both longitudinally opposing ends of the bag 10. i.e., at two positions which are most separate from each other. As shown in FIG. 5(a), the attachment means 2d is provided at two positions along the upper peripheral portion of the bag 10 parallel to the longitudinal direction of the bag 10, and the attachment means 2e is provided at two positions along the lower peripheral portion of the bag 10 parallel to the longitudinal direction of the bag 10. If desired, an additional attachment means may be provided on the vertical centerline L. These arranged attachment means 2c, 2d, and 2e attach the heat and steam generating device 1 to a wearer's body in a stable manner.

The heat generating elements 20a and 20b are fixed at their respective central portions, on their side facing the second stretch sheet 12, to the second stretch sheet 12. The fixing parts are indicated by the reference numerals 3a and 3b. Fixing parts 3a or 3b are provided per heat generating elements 20a or 20b, respectively. The heat and steam generating device 1 of the present embodiment easily folds in half about the centerline L as a folding line. Easily bending inward and outward about the centerline L, the heat and steam generating device 1 is easy to attach to either the inner or the outer side of a joint of an elbow, a knee, etc. To take more advantage of this effect, it is preferable to form a straight slit 15 or perforations 16 along the centerline L of the bag 10. The slit 15 or the perforations 16 make the heat generating elements 20a and 20b to separate apart from each other easily, thereby helping the heat and steam generating device 1 to smoothly comfort to the bending of the joint. The heat and steam generating device 1 of the present embodiment has the advantage of conformability particularly to a twisting movement. The straight slit 15 may be replaced with a line of discrete short slits, parallel slits, or at least one elongated hole, such as an elongated rhombus, an elongated rectangle or an elongated oval.

Figure 6A:
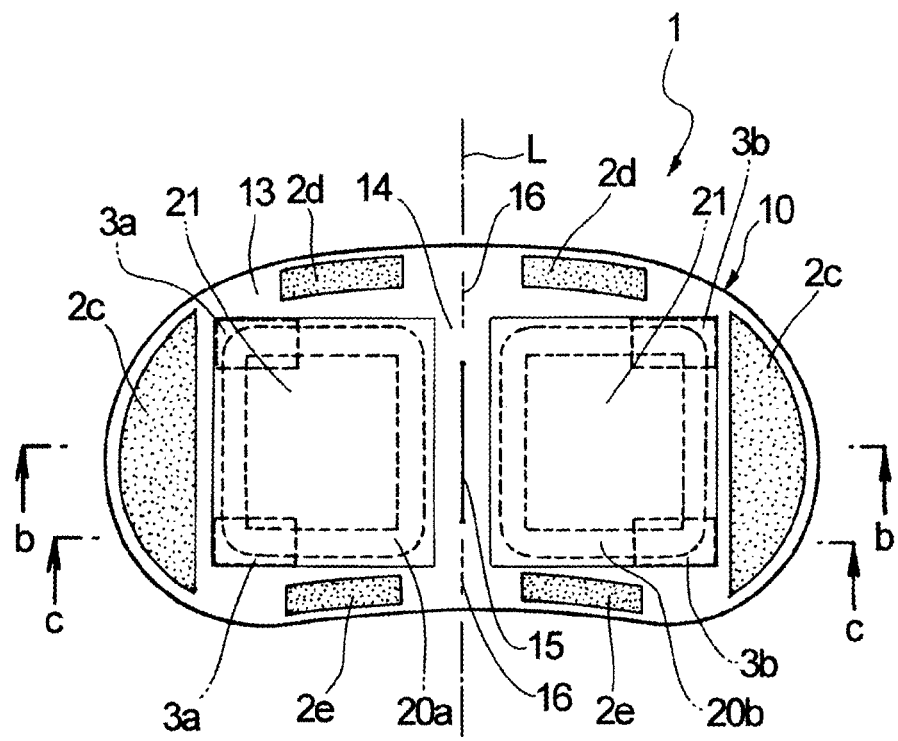
FIG. 6($a$) is a plan of a heat and steam generating device as a third embodiment of the heat generating device of the invention, FIG. 6($b$) is a cross-section taken along line b-b in FIG. 6($a$), and FIG. 6($c$) is a cross-section taken along line c-c in FIG. 6($a$).
Figure 6B:
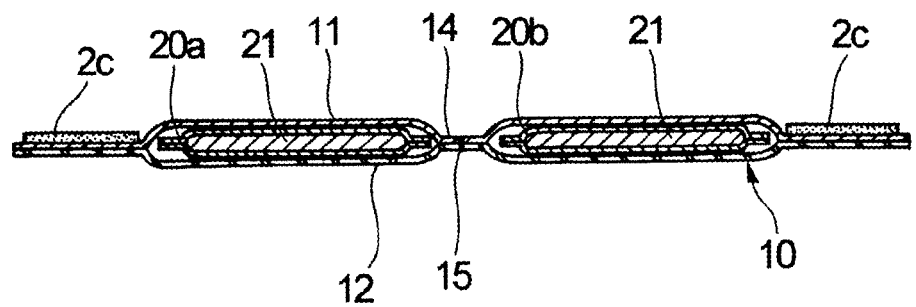
Figure 6C:
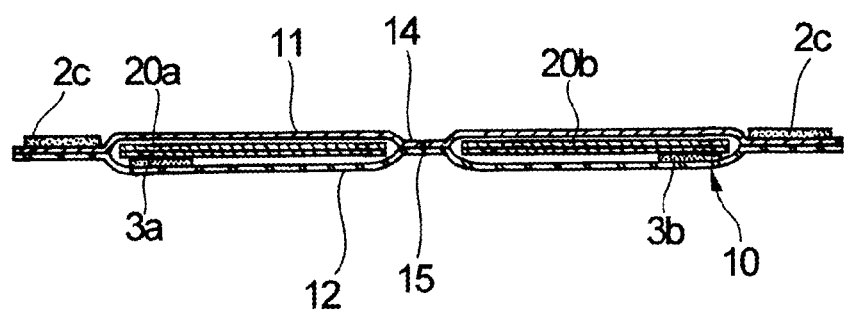

The heat and steam generating device 1 of the third embodiment illustrated in FIG. 6 is different from the second embodiment in terms of the position and number of the fixing parts for fixing the heat generating elements. Specifically, a pair of fixing parts 3a and a pair of fixing parts 3b are provided for the heat generating elements 20a and 20b respectively, and the fixing parts in the same pair are located away from each other. The two pairs of fixing parts 3a and 3b are situated at positions in the heat generating elements 20a and 20b most distant from the vertical centerline L perpendicular to the predominant extensible direction of the bag 10 (i.e., the horizontal direction of the drawing). The line connecting the pair of the fixing parts 3$a$ and the line connecting the pair of the fixing parts 3$b$ intersect, preferably at right angles, with the predominant extensible direction of the bag 10 (i.e., the horizontal direction of the drawing). The line connecting the pair of the fixing parts 3$a$ and the line connecting the pair of the fixing parts 3$b$ intersecting with the predominant extensible direction of the bag 10, the stretchability of the bag 10 is hardly impaired. According to the present embodiment, the bag 10 has a large stretchable portion in its central portion so that the heat and steam generating device 1 sufficiently conforms to the bending of a joint to which it is attached.

Figure 7A:
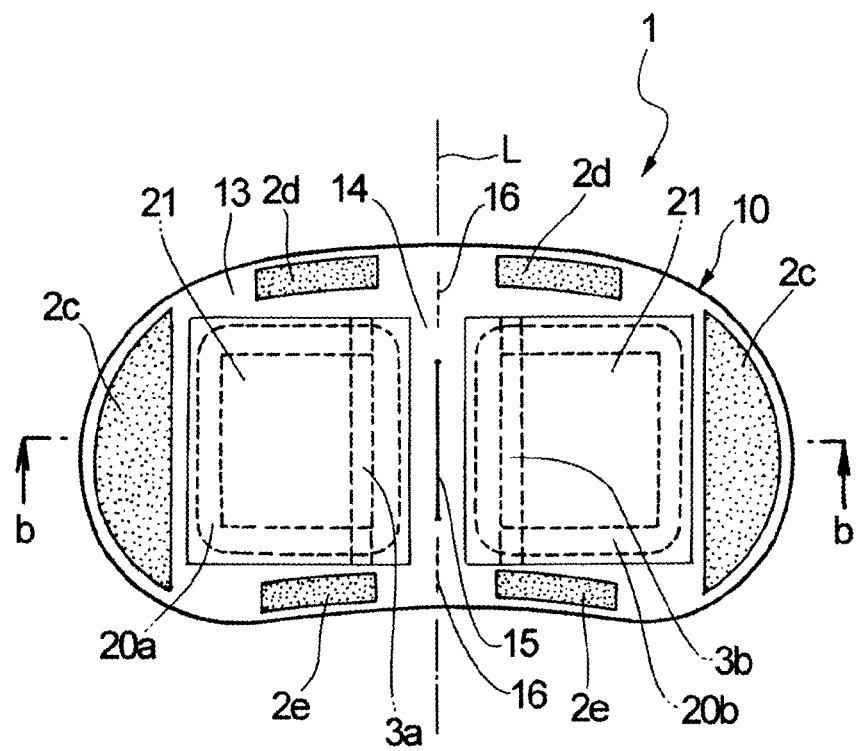
FIG. 7 is a plan of a heat and steam generating device as a fourth embodiment of the heat generating device of the invention, and FIG. 7($b$) is a cross-section taken along line b-b in FIG. 7($a$).
Figure 7B:
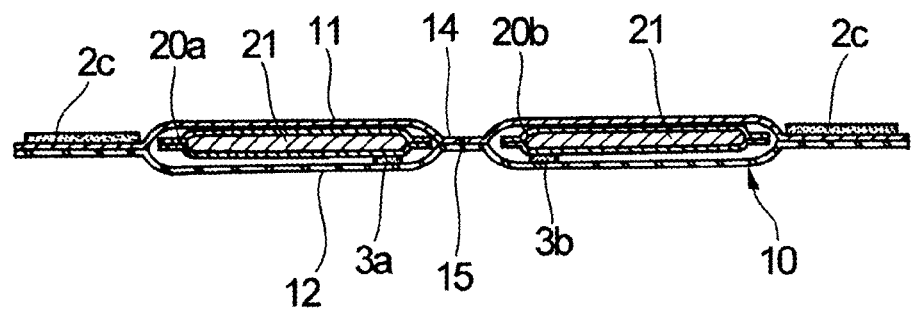

The heat and steam generating device 1 according to the fourth embodiment illustrated in FIG. 7 has the same number of the fixing parts as in the second embodiment (one fixing part is provided per heat generating element), but differs in the position and shape of the fixing parts from the second embodiment. Specifically, each of the fixing parts 3$a$ and 3$b$ has an anisotropic rectangular shape with a longitudinal direction and a transverse direction, the longitudinal direction intersecting, preferably at right angles, with the predominant extensible direction of the bag 10 (i.e., the horizontal direction of the drawing). The fixing parts 3$a$ and 3$b$ are each situated at a position in the respective heat generating elements 20$a$ and 20$b$ closest to the vertical centerline L perpendicular to the predominant extensible direction of the bag 10 (i.e., the horizontal direction of the drawing) as opposed to the arrangement of the third embodiment of FIG. 6, in which the fixing parts 3$a$ and 3$b$ are located most distant from the vertical centerline L. As seen from the above, in the case where a plurality of heat generating elements are enclosed in a bag, whether the opposite fixing parts of the adjacent heat generating elements are arranged to be separate from each other (e.g., as in the third embodiment) or close to each other (e.g., as in the fourth embodiment) can be chosen as appropriate to facilitate effective conformation of the heat and steam generating device 1 to a wearer's body.

Figure 8A:
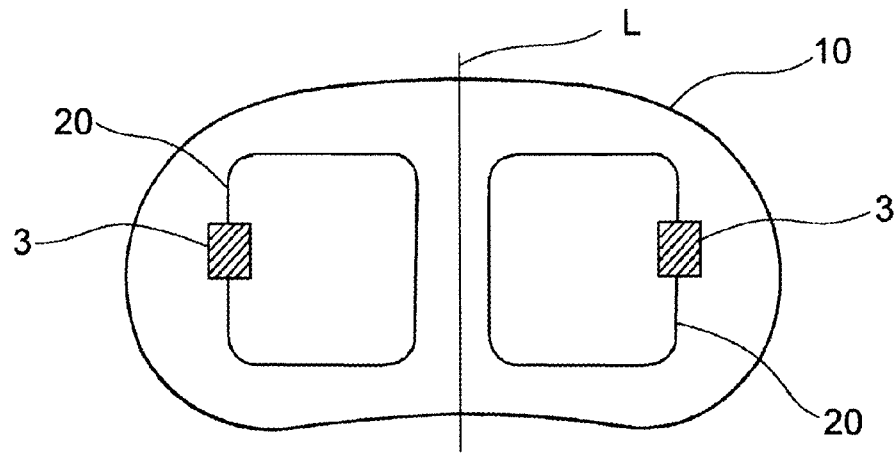
FIG. 8($a$), FIG. 8($b$), and FIG. 8($c$) are each a plan showing the shapes and positions of fixing parts.
Figure 8B:
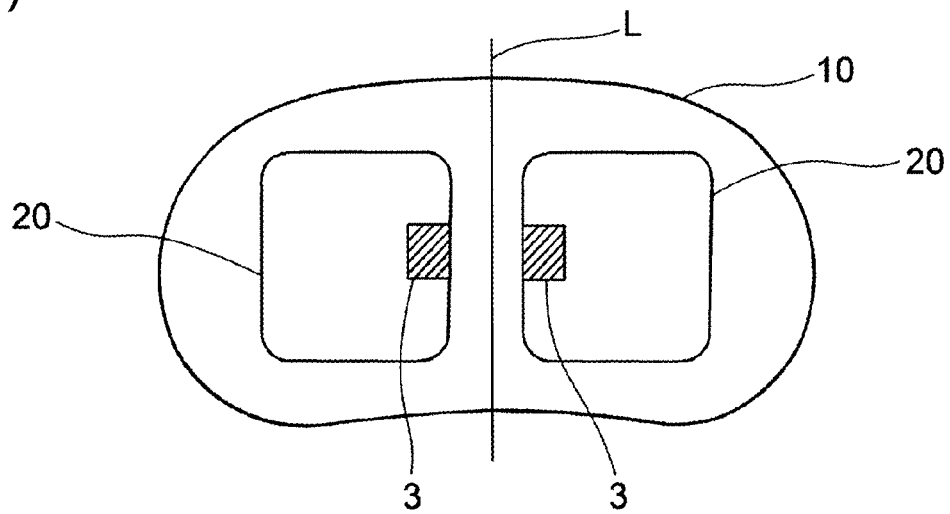
Figure 8C:
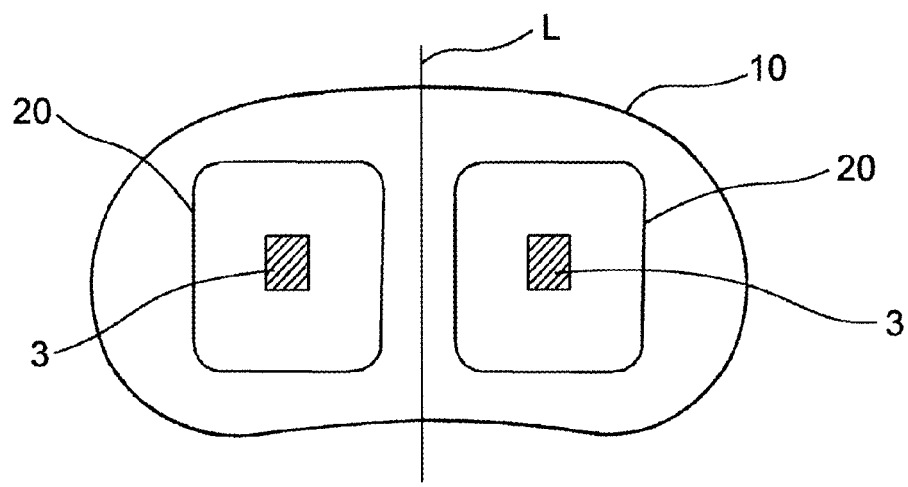

FIGS. 8 through 12 illustrate a variety of the configurations, inclusive of the shape and position, of the fixing parts 3. FIGS. 8($a$) to 8($c$) show the shape and positions of fixing parts 3 that are suitable where the bag 10 is nearly equally stretchable in the longitudinal and transverse directions. In FIG. 8($a$) a rectangular fixing part 3 is situated on each heat generating element 20 at a position most distant from the vertical centerline L. In FIG. 8($b$) a fixing part is situated on each heat generating element 20 at a position closest to the vertical centerline L. In FIG. 8($c$) a fixing part 3 is formed at substantially the center of each heat generating element 20.

Figure 9A:
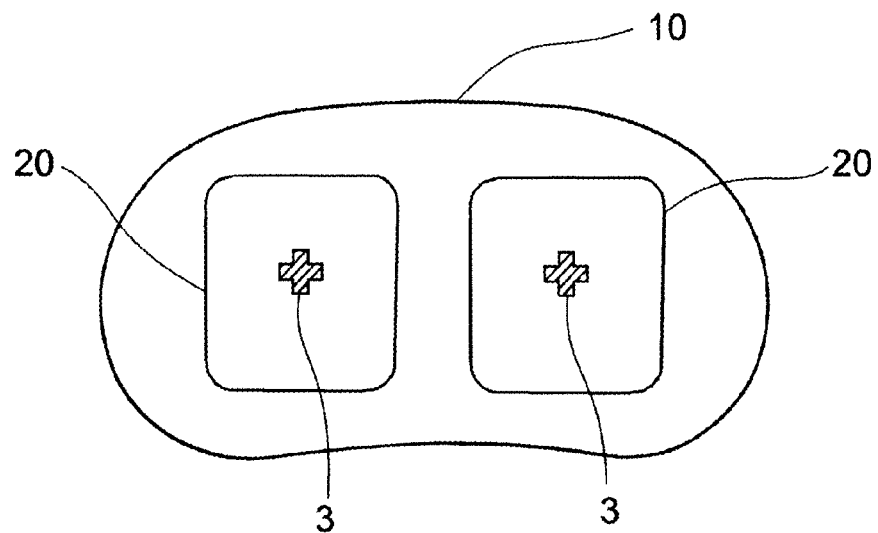
FIG. 9($a$) and FIG. 9($b$) are each a plan showing the shapes and positions of fixing parts.
Figure 9B:
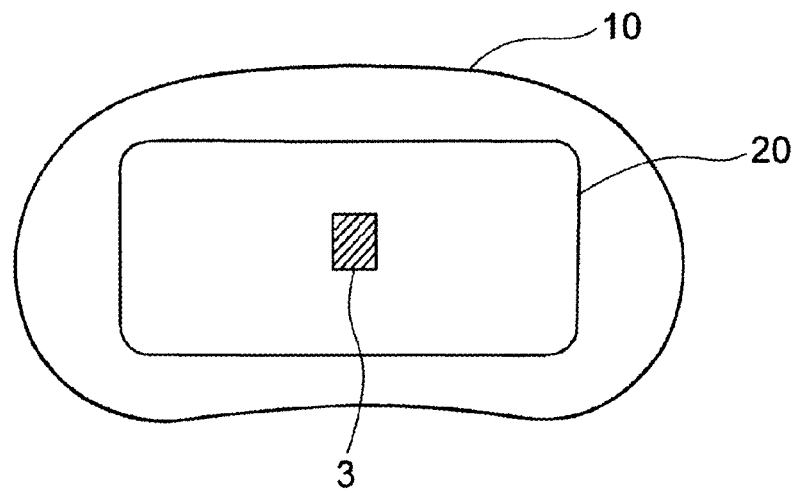

Similarly to the configurations of FIG. 8, the configuration illustrated in FIGS. 9($a$) and 9($b$) are applied to the case where the bag 10 is nearly equally stretchable in the longitudinal and transverse directions. The fixing parts 3 of FIG. 9($a$) are the same in arrangement but different in shape from the configuration of FIG. 8($c$). The fixing parts 3 of FIG. 9($a$) are cross-shaped. When a fixing part 3 is positioned at substantially the center of the heat generating element 20, although the shape of the fixing part 3 is not particularly limited, the shape of a cross is the most effective for preventing displacement, with the area being equal. FIG. 9($b$) displays a configuration where only one heat generating element 20 is used. In FIG. 9($b$), a rectangular fixing part 3 is provided in substantially the center of the heat generating element 20.

Figure 10A:
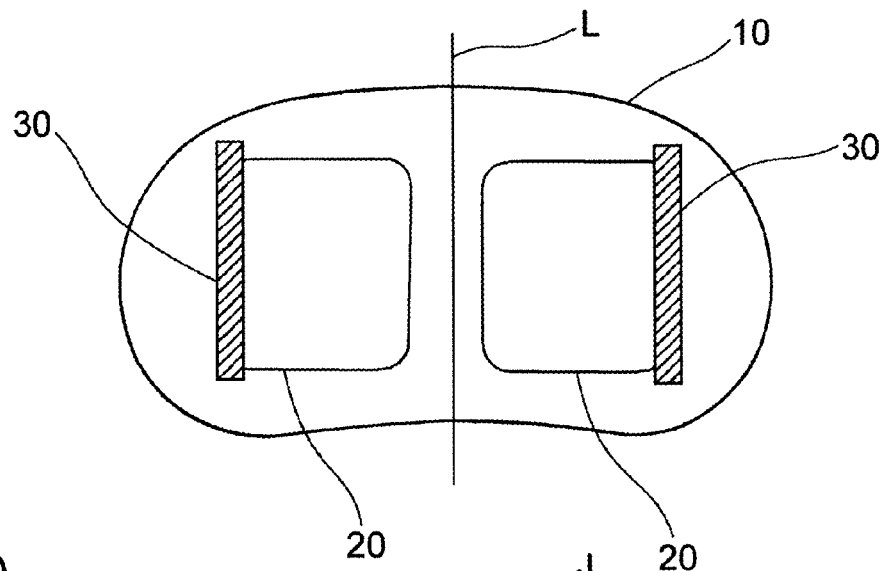
FIG. 10($a$), FIG. 10($b$), and FIG. 10($c$) are each a plan showing the shapes and positions of fixing parts.
Figure 10B:
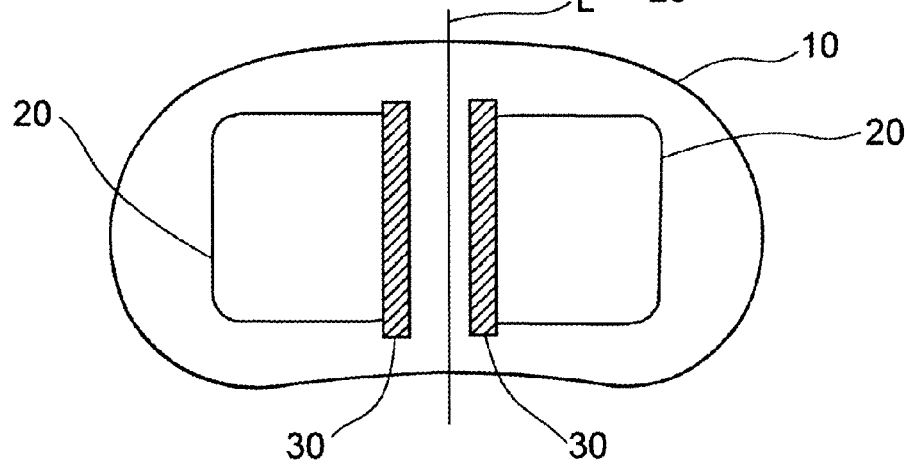
Figure 10C:
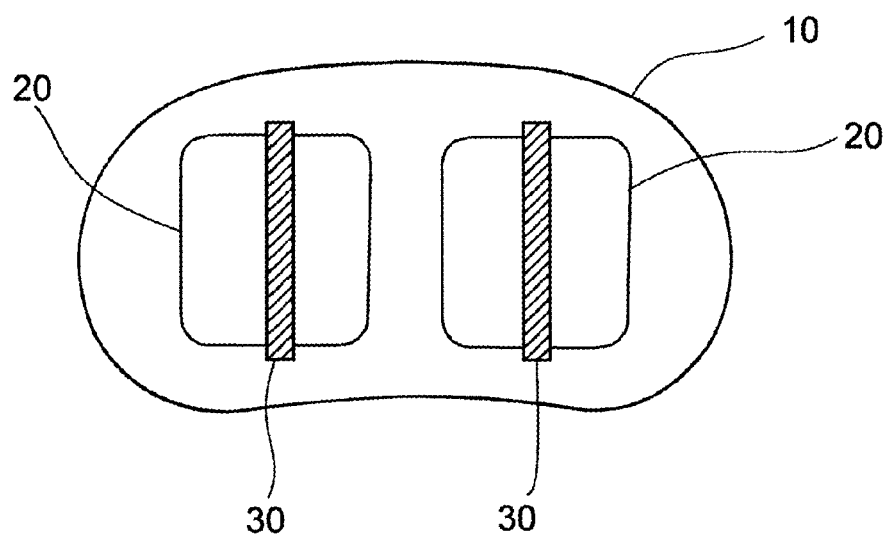

FIGS. 10($a$) to 10($c$) show the shape and positions of fixing parts 3 that are suitable where the bag 10 has anisotropic in stretch directionality. Specifically, the bag 10 is more stretchable in the longitudinal direction than in the transverse direction. In FIG. 10($a$), a continuous fixing part or a plurality of discrete fixing parts is/are provided within each of regions 30. The regions 30 are located on the respective heat generating elements 20 at positions most distant from the vertical centerline L. The regions 30 extend in the transverse direction of the bag 10. In FIG. 10($b$), too, a continuous fixing part or a plurality of discrete fixing parts is/are provided within each of regions 30. The regions 30 are located on the respective heat generating elements 20 at positions closest to the vertical centerline L. The regions 30 extend in the transverse direction of the bag 10. In FIG. 10($c$), too, a continuous fixing part or a plurality of discrete fixing parts is/are provided within each of regions 30. Each region 30 extends in the transverse direction of the bag 10, passing through substantially the center of each heat generating element 20.

Figure 11:
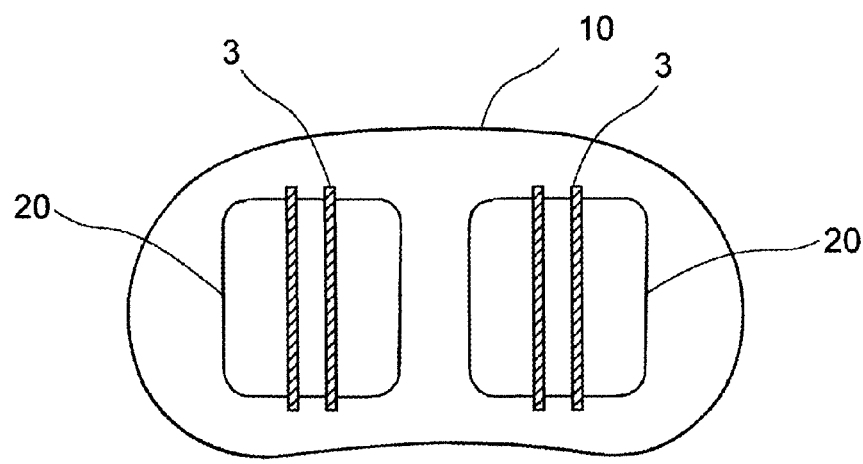
FIG. 11 is a plan showing the shapes and positions of fixing parts.

FIG. 11 shows a configuration applied to the case where the bag 10 is more stretchable in the longitudinal direction than in the transverse direction similarly to the case of FIG. 10. In this configuration, a plurality of strip-shaped fixing parts 3 extending in the transverse direction of the bag 10 are arranged across each heat generating element 20 at a prescribed interval.

Figure 12A:
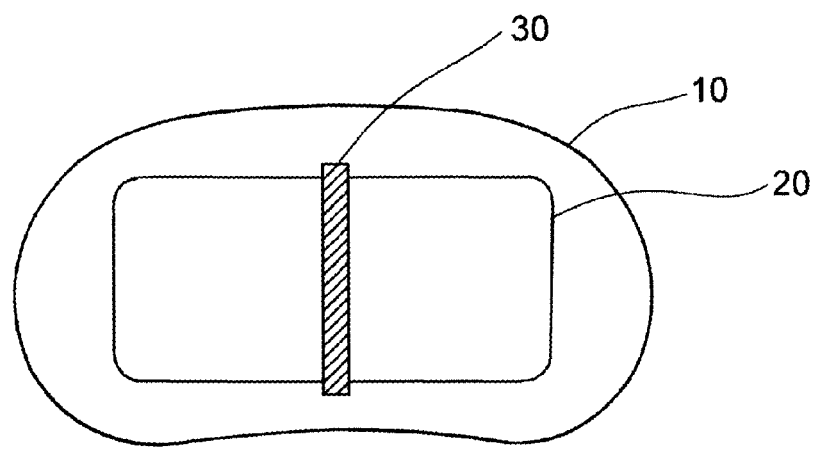
FIG. 12($a$) and FIG. 12($b$) are each a plan showing the shapes and positions of fixing parts.
Figure 12B:
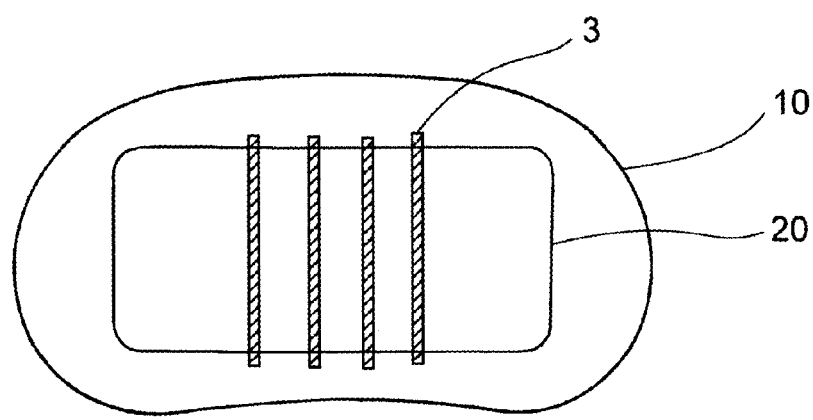

FIGS. 12($a$) and 12($b$) each show a configuration applied to the case where the bag 10 is more stretchable in the longitudinal direction than in the transverse direction similarly to the case of FIG. 10. The configurations of FIG. 12 have one heat generating element 20. In FIG. 12($a$), a continuous fixing part or a plurality of discrete fixing parts is/are provided within a region 30. The region 30 passes through substantially the longitudinal center of the heat generating element 20 and extends in the transverse direction of the bag 10. In FIG. 12($b$), a plurality of strip-shaped fixing parts 3 extending in the transverse direction of the heat generating element 20 are arranged across the heat generating element 20 at a prescribed interval.

In each of the configurations shown in FIGS. 8 through 12, the fixing part can be provided between the heat generating element 20 and the first stretch sheet 11 or the second stretch sheet 12 making the bag 10. Preferably, the fixing part is provided between the heat generating element 20 and the second stretch sheet 12.

Figure 13:
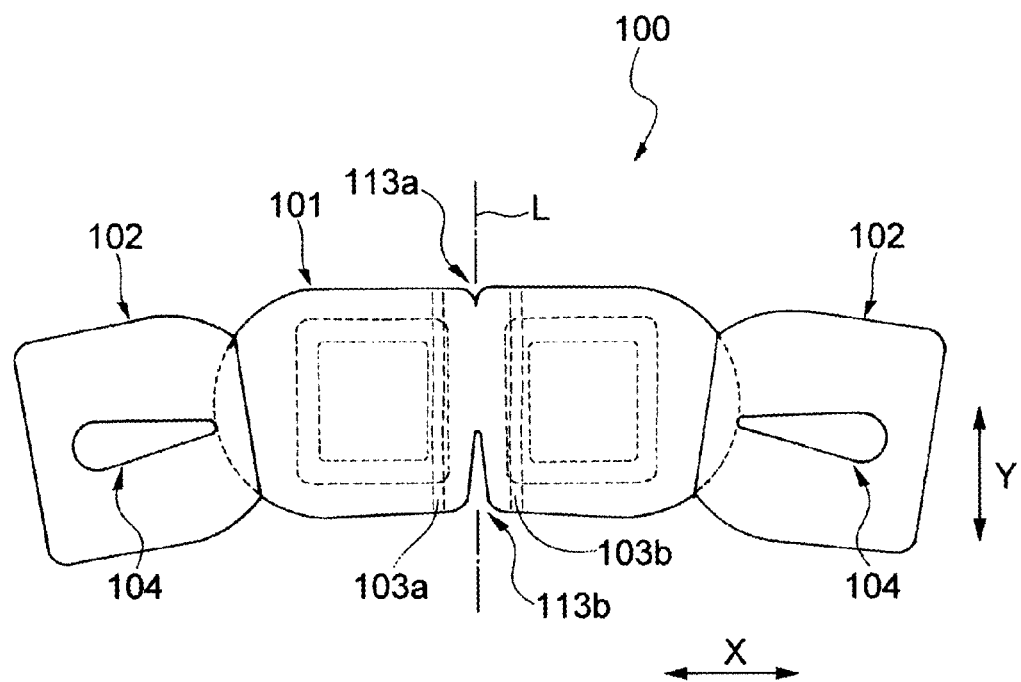
FIG. 13 is a plan of a heat and steam generating device as a fifth embodiment of the heat generating device of the invention.

FIG. 13 illustrates a heat and steam generating device 100 according to the fifth embodiment, which is a heat generating device of eye-mask type unlike the foregoing embodiments. The heat and steam generating device 100 includes a main body 101 and an ear loop 102. The main body 101 has a generally elongated circular shape with longitudinal direction X and transverse direction Y perpendicular to direction X. The ear loop 102 is used as an opposing pair. The pair of ear loops 102 are attached to both longitudinal ends of the main body 101. On use, the ear loops 102 of the heat and steam generating device 100 are looped over the ears of a wearer to cover the wearer's eyes with the main body 101. During wear, the steam generated from the heat and steam generating device 100 is applied to the wearer's eyes, thereby alleviating eye fatigue, eye redness, or eye strain and making the wearer feel relaxed.

Figure 14:
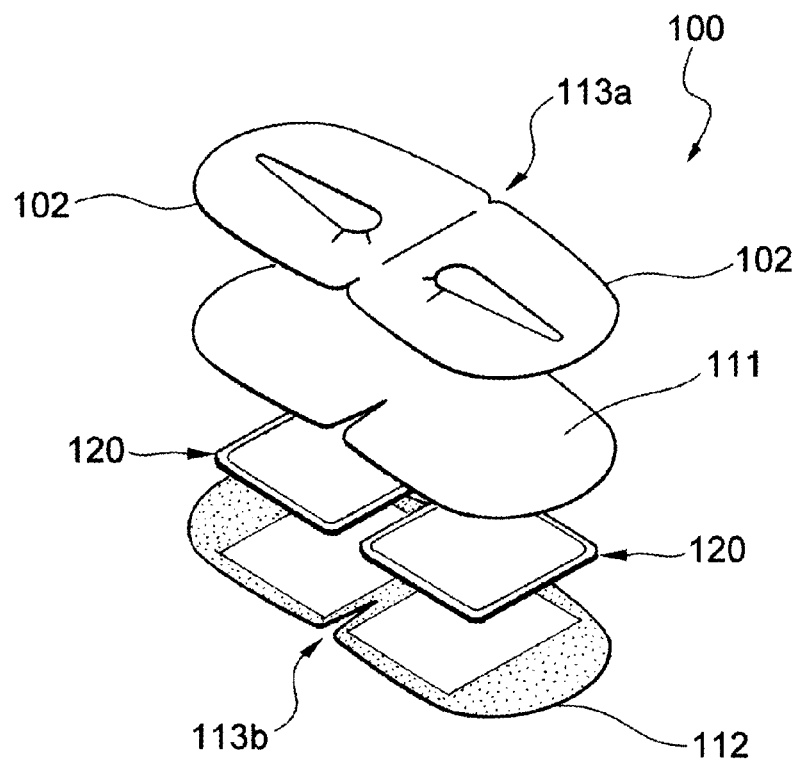
FIG. 14 is an exploded perspective of the heat and steam generating device according to the embodiment shown in FIG. 13.
Figure 15:
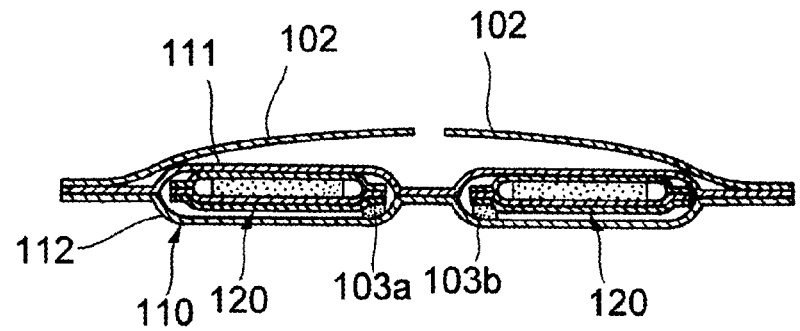
FIG. 15 is a cross-section of the heat and steam generating device of the embodiment shown in FIG. 13 under the state that the ear loops are folded, taken along the longitudinal direction.

FIG. 14 is an exploded perspective view of the heat and steam generating device 100. In this figure, the ear loops 102 are placed on the main body 101. FIG. 15 is a cross-section of the heat and steam generating device 100 taken along direction X. The main body 101 of the heat and steam generating device 100 is composed mainly of one bag 110 and two heat generating elements 120 both enclosed in the bag 110 in such a manner that the each heat generating element 120 is located on each eye of a wearer.

The bag 110 has a first stretch sheet 111 proximal to the wearer's skin and a second stretch sheet 112 distal to the wearer's skin. The two stretch sheets 111 and 112 have the same elongated circular shape. The outlines of the stretch sheets 111 and 112 define the outline of the main body 101. The bag 110 is formed by superposing the two stretch sheets 111 and 112 on each other, and joining the two sheets along their perimeters where their longitudinally central portion of X direction along in direction Y. Therefore, the bag 110 provides two spaces. The two stretch sheets 111 and 112 can be joined by, for example, using a hot melt adhesive. In the embodiment illustrated in FIG. 14, the region where a hot melt adhesive is applied is indicated with fine dots on the inner side of the second stretch sheet 112 (the side facing the first stretch sheet 111). Using a hot melt adhesive to join the stretch sheets 111 and 112 is less likely to detract from the feel to the touch essentially possessed by the stretch sheets 111 and 112 than using other joining means such as thermal fusion bonding, thereby providing the heat and steam generating device 100 with comfort to wear.

The heat and steam generating device 100 having the stretchable main body 101 provides a wearer with not only the advantageous effects produced by the foregoing embodiments but also an additional advantage that the load imposed to the ears by the ear loops 102 is less influenced by the wearer's face size.

The bag 110 has notches 113a and 113b at the midpoint of its two long sides extending in X direction. The notches 113a and 113b are V cuts made inwardly in Y direction from the long sides. The notches 113a and 113b have different depths. When the heat and steam generating device 100 is worn, the notch 113a is located between the wearer's eyebrows or thereabouts, and the notch 113b is located on the nose bridge. Accordingly, the notch 113b is deeper than the notch 113a. Either one or both of the notches 113a and 113b shown in FIG. 13 may be a slit.

Figure 16A:
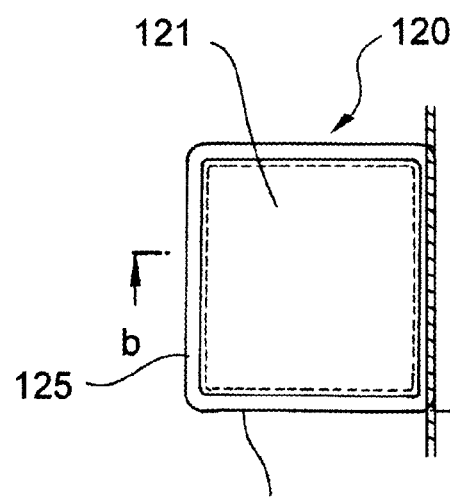
FIG. 16($a$) is a plan of the heat generating element used in the heat and steam generating device of the embodiment shown in FIG. 13, and FIG. 16($b$) is a cross-section taken along line b-b in FIG. 16($a$).
Figure 16B:
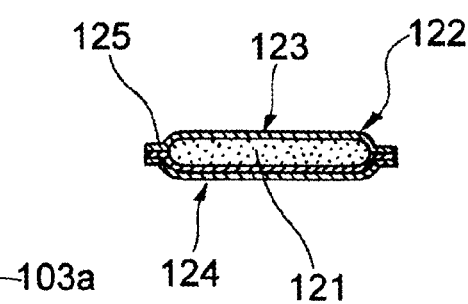

FIGS. 16(a) and 16(b) are a plan and a cross-section, respectively, of the heat generating element 120. The heat generating element 120 is almost square in a plan view. The heat generating element 120 includes a heat generating member 121 and a holder 122 holding the heat generating member 121. The holder 122 is a flat container, and its contour defines the contour of the heat generating element 120. The holder 122 is formed of a plurality of sheet materials joined together to provide a closed space in which the heat generating member 121 is placed. The flat holder 122 has a first side 123 proximal to the skin of a wearer and a second side 124 opposite to the first side 123 and distal to the skin of a wearer.

The sheet materials forming the first side 123 and the second side 124 are joined together along their perimeters to form a peripheral joint 125 of closed loop. The peripheral joint 125 is continuous. The sheet materials forming the first side 123 and the second side 124 are not bonded to each other inside the peripheral joint 125. There is thus provided a single closed space in which the heat generating member 121 is enclosed.

The first side 123 of the holder 122 has air permeability to allow for passage of air and steam. The second side 124 is less air permeable than the first side 123 or air impermeable. In the present embodiment, the first side 123 is formed of a single sheet material, while the second side 124 is formed of a laminate having two sheet materials. The sheet material forming the first side 123 is, for example, a moisture permeable film. The sheet material forming the second side is a laminate composed of, for example, a moisture permeable film that is less permeable to moisture than the moisture permeable film forming the first side 123 or a moisture impermeable film and paper. In this case, paper is disposed to face outside, i.e., to face the second stretch sheet 112.

The paper, one of the sheet materials providing the second side 124, may be scented with a fragrance. Scenting paper is achieved by impregnating paper with a desired fragrance composition alone or together with a diluent or the like. By scenting the heat generating element 120 with a fragrance, vaporization of the fragrance is accelerated by the heat and steam generated during use of the heat and steam generating device 100. Therefore, the scented heat and steam generating device 100 provides a wearer with aromatic relaxation as well as the improvement on physiological functions by the steam and heat.

FIGS. 15 and 16 display the state of the heat generating element 120 fixed to the bag 110. The heat generating members 120 are fixed to the inner side of the second stretch sheet 112 of the bag 110 at fixing parts 103a and 103b. Each of the fixing parts 103a and 103b has an anisotropic shape with a longitudinal direction and a transverse direction, the longitudinal direction intersecting, preferably at right angles, with the predominant extensible direction of the bag 110 (i.e., direction X of the figures). The fixing parts 103a and 103b are situated at positions, in the respective heat generating elements 120, closest to the vertical centerline L perpendicular to the predominant extensible direction (i.e., direction X) of the bag 110 (i.e., direction Y). By forming the fixing parts 103a and 103b at these positions, the heat generating elements 120 are successfully located on the wearer's eyes when the heat and steam generating device 100 is put on while being extended in direction X. It is possible to provide the fixing parts 103a and 103b on the respective heat generating elements 120 at positions most distant from the vertical centerline L (closest to the ear loops 102), in which case, however, the heat generating elements 120 can be located outboard of the eyes depending on the wearer's face size.

When, in particular, the positions of the fixing parts 103a and 103b on the heat generating elements 120 do not overlap the heat generating members 121 in a plan view as illustrated in FIG. 16, the fixing causes still less impairment to the stretchability of the bag 110, and the heat generating elements 120 can successfully be located on the wearer's eyes while the heat and steam generating device 100 is worn.

Until use, the ear loops 102 of the heat and steam generating device 100 are disposed to cover the stretch sheet 111 of the main body 101 as illustrated in FIGS. 14 and 15. Upon use, the ear loops 102 are opened outward along direction X into the state illustrated in FIG. 13. In the state before use, i.e., with the pair of ear loops 102 disposed on the main body 101, the outline delineated by the pair of ear loops 102 is practically the same as the outline of the main body 101.

Figure 17:
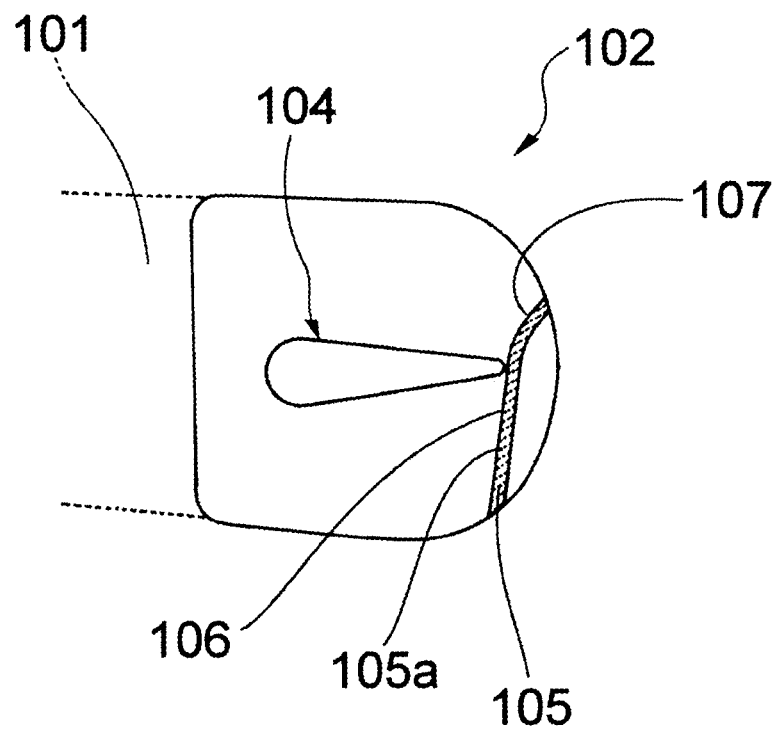
FIG. 17 is an enlarged view of an ear loop of the heat and steam generating device of the embodiment shown in FIG. 13.

FIG. 17 is an enlarged view of one of the ear loops 102. The ear loop 102 illustrated in FIG. 17 is in a state before being opened outward along direction X. The ear loop 102 is formed of a sheet material having an elongated opening 104 extending in direction X. The elongated opening 104 is a generally isosceles triangle with rounded vertices and tapered toward an ear loop joint 105. The elongated opening 104 is located in almost the center in direction Y. The elongated opening 104 is a hole through which a wearer's ear is engaged. The ear loop 102 may have a slit cut from the edge of the opening 104 on the side coming into contact with the ear which is opposed to the joint 105 (see FIG. 14).

The ear loop 102 is joined at its outmost position in direction X to the outer side of the stretch sheet 111 of the main body 101. The ear loop 102 and the main body 101 are joined at the joint 105. In opening the ear loop 102 inside out in direction X and putting it around the ear, the joint 105 functions as a folding part for opening the ear loop 102 inside out. The folding line of the folding part corresponds to the inner perimeter 105a of the joint 105 in FIG. 17. Therefore, the shape of the inner perimeter 105a is a factor governing the state of the ear loop 102 after being opened inside out. In other words, the shape of the inner perimeter 105a influences the fit of the heat and steam generating device 100 in use. As a result of investigations into a preferred shape of the inner perimeter 105a from that point of view, it has been proved that the inner perimeter 105a is preferably composed of a first segment 106 and a second segment 107 intersecting with the first segment 106. The first segment 106 extends from the lower side of the main body 101 upward and outward. The second segment 107 extends outward with a smaller inclination than that of the first segment 106 to reach the side edge of the main body 101. By forming the joint 105 with a so designed inner perimeter 105a, the heat and steam generating device 100 is flexibly conformable to any size of the face of a wearer and provides good comfort during wear while being prevented from sliding down irrespective of the wearer's face size. From this viewpoint, the intersecting point between the first segment 106 and the second segment 107 is preferably on or near the extension line from the elongated opening 104.

As mentioned with respect to the fifth embodiment, the heat generating device of the invention including the first to fifth embodiments may be used in combination with a fragrance composition, such as essential oil or a fragrant component, for the purpose of inducing a relaxed, refreshed or sleepy feeling or the like. Volatilization of a fragrance composition combined with the heat generating device of the invention is promoted by the heat and steam generation. As a result, the heat generating device brings about an enhanced relaxing effect by the fragrance as well as the physiological function improving effect by the heat and steam.

Scenting may be achieved by, for example, using various fragrance compositions as such, as dissolved in, e.g., a diluent, or as supported on a medium, e.g., a porous powder. A fragrance composition may be mixed into the heat generating element or infiltrated into the holder or a sheet of the bag. A medium, such as a powder or a sheet, having a fragrance composition supported thereon or infiltrated therein may be put in the bag together with the heat generating element.

In order to adequately release the fragrance from the fragrance composition and to effectively prevent the fragrance from changing, the fragrance composition is preferably applied between the stretch sheet (12 or 112) of the bag (10 or 110) distal to the skin and the heat generating element (20 or 120). Scenting the heat generating device is more preferably achieved by (a) applying the fragrance composition to the sheet material disposed on the second side of the heat generating element (the side distal to the skin) as mentioned with respect to the fifth embodiment or (b) disposing a scented sheet prepared by impregnating a sheet material with a fragrance composition either as such or as diluted with a diluent or the like between the second stretch sheet of the bag and the heat generating element in a non-fixed state or as slightly fixed to the second stretch sheet or the heat generating element not to get out of position. The sheet material to which the fragrance composition is applied can be conventional paper made mainly of wood pulp. Any other sheet materials which can be scented, such as those made of fibrous materials including nonwoven fabrics and woven fabrics, porous films, and moisture- or oil-absorbing sheets, are also usable.

The fragrance composition is used in an amount preferably of 0.005 to 0.06 g, more preferably of 0.007 to 0.045 g, per gram of the solids content of the heat generating member 121 to produce sufficiently satisfactory results.

While the present invention has been described with respect to its preferred embodiments, it should be understood that the invention is not construed as being limited thereto. For example, while the heat and steam generating devices 1 illustrated in FIGS. 1 through 7 are designed to be attached to a part of body of a wearer, they may be used as attached to a wearer's garment. In the case where the heat and steam generating device 1 is attached to a garment, a fixing means such as an adhesive is provided on the surface of the second stretch sheet 12 of the bag 10. A heat and steam generating device having such a structure may be attached to the inner side (the side facing the skin) of the front portion of sanitary panties, in which application ease of menstrual cramps is expected.

While the bag 10 used in the embodiments shown in FIGS. 1 through 7 has a generally rhombic shape or a generally kidney bean shape, the shape of the bag 10 is not limited thereto and may be circular, oval, rectangular, etc.

While the heat and steam generating device of the embodiment shown in FIG. 13 has ear loops 102 formed of a sheet material, the ear loops may be formed of a rubber string.

While the foregoing embodiments relate to application of the heat generating device of the present invention to a heat and steam generating device, the invention is also applicable to other heat generating implements, including those known as disposable body warmers or heating pads capable of generating heat without being accompanied by substantial steam generation.

EXAMPLES

The present invention will now be illustrated in greater detail by way of Examples, but the invention is not deemed to be limited thereto. Unless otherwise noted, all the percents and parts are by weight.

Production of Heat and Steam Generating Device

A heat and steam generating device 100 having the structure illustrated in FIGS. 13 through 17 was made in accordance with the following procedures (1) to (3).

(1) Preparation of Heat Generating Sheet 121

Raw Material Formulation:

(a) Oxidizable metal: iron powder (RKH (trade name) available from Dowa Iron Powder Co., Ltd. 83%

(b) Fibrous material: pulp fiber NBKP (Mackenzie (trade name) available from Fletcher Challenge Canada, Ltd.; CSF: adjusted to 150 ml) 8%

(c) Activated carbon: Carboraffin (trade name) available from Japan EnviroChemicals, Ltd. (average particle size: 45 μm) 9%

To the mixture of components (a), (b), and (c) were added 0.7 parts of a polyamide-epichlorohydrin resin (WS4020 from Seiko PMC Corp.) as a cationic flocculant and 0.18 parts of a sodium carboxymethyl cellulose (HE 1500F from Dai-ichi Kogyo Seiyaku Co., Ltd.) as an anionic flocculant per 100 parts of the solids content of the mixture (i.e., the total of components (a) to (c)). Industrial water was added to the mixture to prepare a slurry having a solids concentration of 12%.

Papermaking Conditions

The thus prepared slurry was diluted with water to 0.3% in front of the head box and drained on an inclined short-wire paper machine at a line speed of 15 m/min to form a wet paper web.

Drying Conditions

The paper web was dewatered between felt blankets, passed as such between 140° C. heated rollers to be dried to a water content of 5% or less. The dried sheet had a basis weight of 450 g/m² and a thickness of 0.45 mm. As a result of measurement with a thermogravimetric analyzer (TG/DTA 6200 from Seiko Instruments Inc.), the resulting sheet was found to be made up of 83% iron, 9% activated carbon, and 8% pulp.

Preparation of Heat Generating Sheet 121

An electrolyte having the following composition was syringed into the resulting sheet and made to spread throughout the sheet by capillarity to make square heat generating sheets 121 measuring 49 mm by 49 mm each containing 42 parts of the electrolyte per 100 parts of the sheet. All the operations after the addition of the electrolyte were performed in a nitrogen atmosphere.

Electrolyte

Supporting electrolyte: purified salt (NaCl)
Water: industrial water
Electrolyte concentration: 5%

(2) Preparation of Heat Generating Element 120

A porous, moisture permeable, calcium carbonate-containing polyethylene film (air permeance: 2,500 sec) was used to form the first side 123 of a holder 122. A moisture impermeable polyethylene film laminated with tissue paper by an adhesive was used to form the second side 124. The film as the first side and the laminate film as the second side were superposed with the tissue paper facing outside, and the heat generating sheet 121 was interposed therebetween. The film as the first side and the laminate film as the second side were joined along their perimeters to make a rectangular heat generating element 120. The tissue paper was impregnated with 0.017 g of a fragrant component per 1.08 g of the solids content of the heat generating member 121.

(3) Preparation of Heat and Steam Generating Device 100

Two heat generating elements 120 prepared above were sandwiched between polyethylene terephthalate nonwoven fabrics (needle-punched; basis weight: 100 g/m²; thickness 0.72 mm; available from Kureha Tech Co., Ltd.) as first and second stretch sheets 111 and 112 as illustrated in FIG. 14. The stretch sheets 111 and 112 were joined to each other along their peripheral portions, and each of the heat generating elements 120 was fixed to the second stretch sheet 112 at positions indicated by reference numerals 103a and 103b in FIGS. 13 and 15. As illustrated in FIG. 14, a pair of ear loops 102 was affixed to the outer side of the first sheet 111 to provide a desired heat and steam generating device 100. All the above operations were conducted in an oxygen-free atmosphere. The stretch sheets 111 and 112 were stretchable in direction X indicated in FIG. 13 and had a load at 50% extension of 0.8N/5 cm.

INDUSTRIAL APPLICABILITY

As described in detail, the present invention provides a heat generating device that is highly conformable to the wearer's movement as attached to a wearer's body or garment. Therefore, the heat generating device of the invention provides a good fit and a good usability during wear.

The invention claimed is:

1. A heat generating eye mask comprising:
a stretch bag that is air-permeable and a heat generating element enclosed in the stretch bag, a length of the stretch bag being greater than a width of the stretch bag,
the stretch bag including a first stretch sheet that is to be provided proximal to a wearer and a second stretch sheet that is to be provided distal to the wearer relative to the first stretch sheet of the stretch bag,
the heat generating element having a first side which is air-permeable and adapted to be located more proximally to the wearer, a second side which is adapted to be located more distally to the wearer, and a heat generating member interposed between the first and second sides, and
the heat generating element being fixed to an inner side of the second stretch sheet of the stretch bag via a fixing part, such that stretchability of the stretch bag is not impaired, wherein
the first stretch sheet has a load, at 50% extension, of 5N/2.5 cm or less in its most stretchable direction,
the inner side of the second stretch sheet and the second side of the heat generating element facing the inner side of the second stretch sheet are flat except at their respective perimeters,
the stretch bag has a predefined bendable central joint that divides the stretch bag evenly at a width-wise centerline of the stretch bag that runs in a width direction corresponding to the width of the stretch bag,
in a plan view of the heat generating eye mask, a length of the fixing part, which is greater than a width of the fixing part, extends in the width direction of the stretch bag so as to overlap both a first edge and a second edge opposite the first edge of the heat generating element,
the fixing part is centered about a length-wise centerline of the stretch bag that runs in a length direction corresponding to the length of the stretch bag,
the length-wise centerline is perpendicular to the width-wise centerline of the stretch bag, and
in the plan view of the heat generating eye mask the fixing part is arranged closer to a third edge of the heat generating element than a fourth edge of the heat generating element opposite the third edge, the third edge being closer to the predefined bendable central joint than the fourth edge.

2. The heat generating eye mask according to claim 1, wherein the heat generating element is fixed to the inner side of the second stretch sheet of the stretch bag at only the fixing part.

3. The heat generating eye mask according to claim 2, wherein the fixing part, which is not more than 30%, by area, of the heat generating element from the plan view, is fixed to the inner side of the second stretch sheet of the stretch bag.

4. The heat generating eye mask according to claim 1, wherein the fixing part is located in an overlap area where the stretch bag and the heat generating element overlap with each other in the plan view of the heat generating eye mask, the second stretch sheet of the stretch bag is stretchable at the overlap area where the stretch bag and the heat generating element overlap with each other, and the second stretch sheet of the stretch bag is not stretchable where the fixing part is located in the overlap area.

5. The heat generating eye mask according to claim 1, wherein the stretch bag has an oblong shape and has an ear loop at each longitudinal end of the stretch bag.

6. The heat generating eye mask according to claim 1, wherein:
the heat generating element includes two or more heat generating elements separately enclosed in the stretch bag,
the stretch bag has a straight slit or perforations located between the two or more heat generating elements,
the straight slit or the perforations are provided in a seam of the stretch bag that separates the two or more heat generating elements and that forms a separate compartment for each of the two or more heat generating elements, and
the seam and the straight slit or perforations form the predefined bendable central joint between the separate compartments for the two or more heat generating elements.

7. The heat generating eye mask according to claim 1, wherein the heat generating element is fixed to the inner side of the second stretch sheet of the stretch bag such that the stretchability of the stretch bag is not impaired in an overlap area of the heat generating element and the stretch bag with respect to the plan view of the heat generating eye mask.

8. The heat generating eye mask according to claim 7, wherein the fixing part, which is not more than 20%, by area, of the heat generating element from the plan view, is fixed to the inner side of the second stretch sheet of the stretch bag.

9. The heat generating eye mask according to claim 8, wherein the fixing part, which is not more than 15%, by area, of the heat generating element from the plan view, is fixed to the inner side of the second stretch sheet of the stretch bag.

10. The heat generating eye mask according to claim 1, wherein the load of the first stretch sheet at 50% extension is 3N/2.5 cm or less in its most stretchable direction.

11. The heat generating eye mask according to claim 1, wherein the load of the first stretch sheet at 50% extension is 1N/2.5 cm or less in its most stretchable direction.

12. The heat generating eye mask according to claim 1, wherein the load of the first stretch sheet at 50% extension is 15N/2.5 cm or less in its least stretchable direction.

13. The heat generating eye mask according to claim 1, wherein the load of the first stretch sheet at 50% extension is 10N/2.5 cm or less in its least stretchable direction.

14. The heat generating eye mask according to claim 1, wherein the load of the first stretch sheet at 50% extension is 5N/2.5 cm or less in its least stretchable direction.

15. The heat generating eye mask according to claim 1, wherein the stretch bag includes one or more adhesive parts to attach to the wearer, the one or more adhesive parts provided on the first stretch sheet of the stretch bag.

16. The heat generating eye mask according to claim 1, wherein:
the stretch bag and the heat generating element are fixed to each other according to one of the following arrangements:
the fixing part consisting of only one first fixing part, the only one first fixing part being shaped so as to have anisotropy having a longest dimension to shortest dimension ratio of 5:1 or less; or
the fixing part consisting of a second fixing part located at a first position on the heat generating element adjacent to the width-wise centerline perpendicular to the length-wise centerline, which is a predominant extensible direction of the stretch bag.

17. A heat generating eye mask comprising:
a stretch bag that is air-permeable and a heat generating element enclosed in the stretch bag, a length of the stretch bag being greater than a width of the stretch bag,
the stretch bag including a first stretch sheet that is to be provided proximal to a wearer and a second stretch sheet that is to be provided distal to the wearer relative to the first stretch sheet of the stretch bag,
the heat generating element having a first side which is air-permeable and adapted to be located more proximally to the wearer, a second side which is adapted to be located more distally to the wearer, and a heat generating member interposed between the first and second sides,
the heat generating element being fixed to an inner side of the second stretch sheet of the stretch bag via a fixing part, such that stretchability of the stretch bag is not impaired, and
the heat generating device being scented with a fragrance component, wherein
the first stretch sheet has a load, at 50% extension, of 5N/2.5 cm or less in its most stretchable direction,
the inner side of the second stretch sheet and the second side of the heat generating element facing the inner side of the second stretch sheet are flat except at their respective perimeters,
the stretch bag has a central joint that divides the stretch bag at a width-wise centerline of the stretch bag that runs in a width direction corresponding to the width of the stretch bag,
in a plan view of the heat generating eye mask, a length of the fixing part, which is greater than a width of the fixing part, extends in the width direction of the stretch bag so as to overlap both a first edge and a second edge opposite the first edge of the heat generating element,
the fixing part is centered about a length-wise centerline of the stretch bag that runs in a length direction corresponding to the length of the stretch bag,
the length-wise centerline is perpendicular to the width-wise centerline of the stretch bag, and,
in the plan view of the heat generating eye mask the fixing part is arranged closer to a third of the heat generating element than a fourth edge of the heat generating element opposite the third edge, the third edge being closer to the central joint than the fourth edge.

18. The heat generating eye mask according to claim 17, wherein:
the stretch bag and the heat generating element are fixed to each other according to one of the following arrangements:
the fixing part consisting of only one first fixing part located at a virtual center inward of a periphery of the heat generating element, and the only one first fixing part is shaped so as to have no anisotropy or anisotropy having a longest dimension to shortest dimension ratio of 5:1 or less; or
the fixing part consisting of a second fixing part located at a first position on the heat generating element closest to the width-wise centerline perpendicular to the length-wise centerline, which is a predominant extensible direction of the stretch bag; or
the fixing part consisting of a third fixing part located at a second position on the heat generating element most distant from the width-wise centerline perpendicular to the length-wise centerline, which is the predominant extensible direction of the stretch bag.

19. A heat generating eye mask comprising:
a stretch bag that is air-permeable and two or more heat generating elements separately enclosed in the stretch bag, a length of the stretch bag being greater than a width of the stretch bag,
the stretch bag including a first stretch sheet that is to be provided proximal to a wearer and a second stretch sheet that is to be provided distal to the wearer relative to the first stretch sheet of the stretch bag,
each of the two or more heat generating elements having a first side which is air-permeable and adapted to be located more proximally to skin of the wearer, a second side which is adapted to be located more distally to the skin, and a heat generating member interposed between the first and second sides, and
each of the two or more heat generating elements being fixed to an inner side of the second stretch sheet of the stretch bag via respective fixing parts, such that stretchability of the stretch bag is not impaired, wherein
the stretch bag has a straight slit or perforations located between the two or more heat generating elements,
the straight slit or the perforations are provided in a seam of the stretch bag that separates the two or more heat generating elements and that forms a separate compartment for each of the two or more heat generating elements,
the seam and the straight slit or perforations form a predefined bendable central joint between the separate compartment for each of the two or more heat generating elements,
the inner side of the second stretch sheet and each said second side of the two or more heat generating elements facing the inner side of the second stretch sheet are flat except at their respective perimeters,
in a plan view of the heat generating eye mask, each of the fixing parts extends in a width direction of the stretch bag so as to overlap both a first edge and a second edge opposite the first edge of respective ones of the heat generating elements,
each of the fixing parts is centered about a length-wise centerline of the stretch bag that runs in a length direction corresponding to the length of the stretch bag,
the length-wise centerline is perpendicular to a width-wise centerline of the stretch bag that runs in a width direction corresponding to the width of the stretch bag, and
in the plan view of the heat generating eye mask each of the fixing parts is arranged closer to a third edge of the respective ones of the heat generating elements than a fourth edge of the respective heat generating element opposite the third edge, the third edge being closer to the predefined bendable central joint than the fourth edge.

20. The heat generating eye mask according to claim 19, wherein:
the stretch bag and each of the two or more heat generating elements are fixed to each other according to one of the following arrangements:
the fixing part consisting of only one first fixing part per each of the two or more heat generating elements, which is located at a virtual center inward of a periphery of a respective heat generating element of the two or more heat generating elements, and the only one first fixing part per heat generating element is shaped as to have no anisotropy or anisotropy having a longest dimension to shortest dimension ratio of 5:1 or less; or
the fixing part consisting of a second fixing part per each of the two or more heat generating elements, which is located at a first position on a respective heat generating element of the two or more heat generating elements closest to the width-wise centerline perpendicular to the length-wise centerline, which is a predominant extensible direction of the stretch bag; or
the fixing part consisting of a third fixing part per each of the two or more heat generating elements, which is located at a second position on a respective heat generating element of the two or more heat generating elements most distant from the width-wise centerline perpendicular to the length-wise centerline, which is the predominant extensible direction of the stretch bag.

21. A heat generating eye mask comprising:
a stretch bag that is air-permeable and a heat generating element enclosed in the stretch bag, a length of the stretch bag being greater than a width of the stretch bag,
the stretch bag including a first stretch sheet that is to be provided proximal to a wearer and a second stretch sheet that is to be provided distal to the wearer relative to the first stretch sheet of the stretch bag,
the heat generating element having a first side which is air-permeable and adapted to be located more proximally to the wearer, a second side which is adapted to be located more distally to the wearer, and a heat generating member interposed between the first and second sides,
the heat generating element being fixed to an inner side of the second stretch sheet of the stretch bag via a fixing part, such that stretchability of the stretch bag is not impaired, and
the stretch bag including a pair of ear loops at transverse ends of the stretch bag, wherein
the first stretch sheet has a load, at 50% extension, of 5N/2.5 cm or less in its most stretchable direction,
the inner side of the second stretch sheet and the second side of the heat generating element facing the inner side of the second stretch sheet are flat except at their respective perimeters,
the stretch bag has a central joint that divides the stretch bag at a width-wise centerline of the stretch bag that runs in a width direction corresponding to the width of the stretch bag,
in a plan view of the heat generating eye mask, a length of the fixing part extends in the width direction of the stretch bag so as to overlap both a first edge and a second edge opposite the first edge of the heat generating element,
the fixing part is centered about a length-wise centerline of the stretch bag that runs in a length direction corresponding to the length of the stretch bag,
the length-wise centerline is perpendicular to the width-wise centerline of the stretch bag, and,
in the plan view of the heat generating eye mask the fixing part is arranged closer to a third edge of the heat generating element than a fourth edge of the heat generating element opposite the third edge, the third edge being closer to the central joint than the fourth edge.

22. A heat generating eye mask comprising:
a stretch bag that is air-permeable and a heat generating element enclosed in the stretch bag, a length of the stretch bag being greater than a width of the stretch bag, the stretch bag including one or more adhesive parts to attach to a wearer, the one or more adhesive parts provided on a first stretch sheet of the stretch bag that is to be provided proximal to the wearer, the stretch bag further including a second stretch sheet of the stretch bag that is to be provided distal to the wearer relative to the first stretch sheet of the stretch bag, the heat generating element having a first side which is air-permeable and adapted to be located more proximally to skin of the wearer, a second side which is adapted to be located more distally to the skin, and a heat generating member interposed between the first and second sides, and the heat generating element being fixed to an inner side of the second stretch sheet of the stretch bag via a fixing part, such that stretchability of the stretch bag is not impaired, wherein the first stretch sheet has a load, at 50% extension, of 5N/2.5 cm or less in its most stretchable direction, the heat generating element is fixed to the inner side of the second stretch sheet of the stretch bag in such a manner that the stretchability of the stretch bag is not impaired in an overlap area of the heat generating element and the stretch bag with respect to a plan view of the heat generating eye mask, the heat generating element is fixed to a part of the inner side of the second stretch sheet of the stretch bag at only a part of the heat generating element which is not more than 20%, by area, of the heat generating element from the plan view of the heat generating eye mask, the inner side of the second stretch sheet and the second side of the heat generating element facing the inner side of the second stretch sheet are flat except at their respective perimeters, the stretch bag has a predefined central joint that divides the stretch bag evenly at a width-wise centerline of the stretch bag that runs in a width direction corresponding to the width of the stretch bag, in the plan view of the heat generating eye mask, a length of the fixing part extends in the width direction of the stretch bag so as to overlap both a first edge and a second edge opposite the first edge of the heat generating element, the fixing part is centered about a length-wise centerline of the stretch bag that runs in a length direction corresponding to the length of the stretch bag, the length-wise centerline is perpendicular to the width-wise centerline of the stretch bag, and about a length-wise centerline of the heat generating element, and in the plan view of the heat generating eye mask the fixing part is arranged closer to a third edge of the heat generating element than a fourth edge of the heat generating element opposite the third edge, the third edge being closer to the predefined bendable central joint than the fourth edge.

* * * * *